United States Patent
Chait et al.

(10) Patent No.: US 11,422,135 B2
(45) Date of Patent: Aug. 23, 2022

(54) SYSTEMS AND METHODS FOR CHARACTERIZATION OF MOLECULES

(71) Applicant: Analiza, Inc., Bay Village, OH (US)

(72) Inventors: Arnon Chait, Bay Village, OH (US); Boris Y. Zaslavsky, Solon, OH (US)

(73) Assignee: Analiza, Inc., Bay Village, OH (US)

( * ) Notice: Subject to any disclaimer, the term of this patent is extended or adjusted under 35 U.S.C. 154(b) by 707 days.

(21) Appl. No.: 16/273,253

(22) Filed: Feb. 12, 2019

(65) Prior Publication Data
US 2019/0178891 A1 Jun. 13, 2019

Related U.S. Application Data

(63) Continuation of application No. 15/138,538, filed on Apr. 26, 2016, now abandoned, which is a
(Continued)

(51) Int. Cl.
*G01N 33/48* (2006.01)
*G01N 33/50* (2006.01)
(Continued)

(52) U.S. Cl.
CPC ....... *G01N 33/57434* (2013.01); *G01N 33/53* (2013.01); *G01N 33/543* (2013.01);
(Continued)

(58) Field of Classification Search
CPC .. G01N 33/57434; G01N 33/53; G01N 33/68; G01N 33/6803; G01N 33/6845;
(Continued)

(56) References Cited

U.S. PATENT DOCUMENTS

| 5,008,204 A | 4/1991 | Stehling |
| 5,241,072 A | 8/1993 | Colon et al. |

(Continued)

FOREIGN PATENT DOCUMENTS

| WO | WO 99/010522 A1 | 3/1999 |
| WO | WO 00/010674 A1 | 3/2000 |

(Continued)

OTHER PUBLICATIONS

International Search Report dated Dec. 18, 2003 from International Application No. PCT/US2002/036519, filed Nov. 12, 2002.
(Continued)

*Primary Examiner* — Russell S Negin
(74) *Attorney, Agent, or Firm* — Wolf, Greenfield & Sacks, P.C.

(57) ABSTRACT

The present invention generally provides systems and methods for the detection, identification, or characterization of differences between properties or behavior of corresponding species in two or more mixtures comprised of molecules, including biomolecules and/or molecules able to interact with biomolecules, using techniques such as partitioning. The experimental conditions established as distinguishing between the mixtures of the molecules using the systems and methods of the invention can also be used, in some cases, for further fractionation and/or characterization of the biomolecules and/or other molecules, using techniques such as single-step or multiple-step extraction, and/or by liquid-liquid partition chromatography. The methods could also be used for discovering and identifying markers associated with specific diagnostics, and can be used for screening for such markers once discovered and identified during diagnostics screening.

20 Claims, 5 Drawing Sheets

Related U.S. Application Data continuation of application No. 14/049,249, filed on Oct. 9, 2013, now Pat. No. 9,354,229, which is a continuation of application No. 13/316,625, filed on Dec. 12, 2011, now abandoned, which is a continuation of application No. 11/818,911, filed on Jun. 15, 2007, now Pat. No. 8,099,242, which is a continuation-in-part of application No. 11/440,222, filed on May 24, 2006, now abandoned, which is a continuation-in-part of application No. 10/560,373, filed as application No. PCT/US2004/019343 on Jun. 14, 2004, now abandoned.

(60) Provisional application No. 60/561,945, filed on Apr. 14, 2004, provisional application No. 60/478,645, filed on Jun. 12, 2003.

(51) Int. Cl.
| | |
|---|---|
| *G01N 33/574* | (2006.01) |
| *G16B 5/00* | (2019.01) |
| *G16C 20/30* | (2019.01) |
| *G01N 33/53* | (2006.01) |
| *G01N 33/68* | (2006.01) |
| *G16H 50/50* | (2018.01) |
| *G01N 33/543* | (2006.01) |
| *G16B 20/00* | (2019.01) |

(52) U.S. Cl.
CPC ......... *G01N 33/68* (2013.01); *G01N 33/6803* (2013.01); *G01N 33/6842* (2013.01); *G01N 33/6845* (2013.01); *G16B 5/00* (2019.02); *G16C 20/30* (2019.02); *G16H 50/50* (2018.01); *G01N 2333/96441* (2013.01); *G01N 2333/96455* (2013.01); *G16B 20/00* (2019.02)

(58) Field of Classification Search
CPC .......... G16B 5/00; G16B 20/00; G16C 20/30; G16H 50/50
See application file for complete search history.

(56) References Cited

U.S. PATENT DOCUMENTS

| | | | |
|---|---|---|---|
| 5,340,474 | A | 8/1994 | Kauvar |
| 5,734,024 | A | 3/1998 | Zaslavsky |
| 5,769,074 | A | 6/1998 | Barnhill et al. |
| 5,818,231 | A | 10/1998 | Smith |
| 5,948,750 | A | 9/1999 | Garsky et al. |
| 6,136,960 | A | 10/2000 | Chait et al. |
| 6,642,009 | B2 | 11/2003 | Hung |
| 7,011,955 | B1 | 3/2006 | Stemmler et al. |
| 7,100,095 | B2 | 8/2006 | Godse et al. |
| 7,247,498 | B2 | 7/2007 | Godec et al. |
| 7,968,350 | B2 | 6/2011 | Chait et al. |
| 8,099,242 | B2 | 7/2012 | Chait et al. |
| 8,211,714 | B2 | 7/2012 | Chait et al. |
| 9,354,229 | B2 | 5/2016 | Chait et al. |
| 9,678,076 | B2 | 6/2017 | Chait et al. |
| 2001/0016590 | A1 | 8/2001 | Ahotupa et al. |
| 2001/0044431 | A1* | 11/2001 | Rodriguez ............. A61K 31/57 514/179 |
| 2002/0045198 | A1 | 4/2002 | Mikolajczyk |
| 2003/0016224 | A1 | 8/2003 | Chait et al. |
| 2004/0229375 | A1 | 11/2004 | Chait et al. |
| 2004/0236603 | A1 | 11/2004 | Heller et al. |
| 2006/0240416 | A1 | 10/2006 | Banerjee et al. |
| 2006/0255257 | A1 | 11/2006 | Belgovskiy et al. |
| 2006/0269964 | A1 | 11/2006 | Chait et al. |
| 2007/0128618 | A1 | 6/2007 | Chait et al. |
| 2007/0198194 | A1 | 8/2007 | Chait et al. |
| 2008/0050831 | A1 | 2/2008 | Chait et al. |
| 2011/0166028 | A1 | 7/2011 | Bergstrom et al. |
| 2012/0088692 | A1 | 4/2012 | Chait et al. |
| 2014/0065642 | A1 | 3/2014 | Chait et al. |
| 2015/0219655 | A1 | 8/2015 | Chait et al. |
| 2016/0238607 | A1 | 8/2016 | Chait et al. |
| 2020/0209243 | A1 | 7/2020 | Chait et al. |

FOREIGN PATENT DOCUMENTS

| | | | |
|---|---|---|---|
| WO | WO 01/055698 | A1 | 8/2001 |
| WO | WO 03/016883 | A1 | 2/2003 |
| WO | WO 03/042694 | A2 | 5/2003 |
| WO | WO 2004/111655 | A1 | 12/2004 |
| WO | WO 2005/008247 | A2 | 1/2005 |
| WO | WO 2005/008247 | A3 | 1/2005 |
| WO | WO 2006/124100 | A2 | 11/2006 |
| WO | WO 2007/027561 | A2 | 3/2007 |
| WO | WO 2008/005043 | A2 | 1/2008 |

OTHER PUBLICATIONS

Written Opinion dated Apr. 30, 2003 for Application No. PCT/US2002/036519.

International Search Report/Written Opinion, dated Nov. 23, 2004, for PCT/US2004/019343, dated Nov. 23, 2004.

International Preliminary Examination Report dated Oct. 15, 2003 from International Application No. PCT/US2002/026019.

International Search Report for PCT/US2002/026019 dated Oct. 3, 2002.

Written Opinion dated Apr. 30, 2003 from International Application No. PCT/US2002/026019.

International Search Report and Written Opinion for PCT/US2006/048344 dated Apr. 24, 2008.

International Search Report and Written Opinion for Application No. PCT/US2013/054059 dated Dec. 10, 2013.

International Preliminary Report on Patentability for Application No. PCT/US2013/054059 dated Feb. 19, 2015.

[No Author Listed] Program listing of the Society of Biomolecular Screening 2002, Session 2A Technical Program for the 8th Annual SBS Conference & Exhibition, Sep. 22-26, 2002, Netherlands Congress Centre, The Hague, The Netherlands.

[No Author Listed] Program listing of the Well-Characterized Biologies Conference 2002, California Separation Science Society, WCBP 2002, 6th Symposium on the Interface of Regulatory and Analytical Sciences for Biotechnology Health Products, Jan. 27-30, 2002.

[No Author Listed] QSAR Introduction (web pages; last updated Jul. 2, 2007).

Albertsson et al., Separation processes in biotechnology. Aqueous two-phase separations. Bioprocess Technol. 1990;9:287-327.

Andrews et al., Affinity gel electrophoresis as a predicative technique in the fractionation of transgenic sheep milk proteins by affinity aqueous two-phase partitioning. Biotechnol Lett. 2000;22:1349-1353.

Arnoldi et al., Lipophilicity-Antifungal Activity Relationships for Some Isoflavonoid Phytoalexins. J Agric Food Chem. 1990; 38:834-838.

Atkinson et al., Trypsin and a-Chymotrypsin Partitioning in Polyethylene Glycol/Maltodextrin Aqueous-Two-Phase Systems. Food Bioprod. Proc.Jun. 1994;72:106-112.

Baker et al., In biomarkers we trust? Nat Biotechnol. Mar. 2005;23(3):297-304.

Bast et al., Translational crossroads for biomarkers. Clin Cancer Res. Sep. 1, 2005;11(17):6103-8.

Berggren et al., Substitutions of surface amino acid residues of cutinase probed by aqueous two-phase partitioning. BBA. 2000;1481:317-327.

Bevan et al., A High-Throughput Screening Method for the Determination of Aqueous Drug Solubility Using Laser Nephelometry in Microtiter Plates. Anal. Chem. 2000;72:1781-1787.

Bodnar et al. Exploiting the Complementary Nature of LC/MALDI/MS/MS and LC/ESI/MS/MS for Increased Proteome Coverage. American Society for Mass Spectrometry. 2003;14:971-979.

(56) References Cited

OTHER PUBLICATIONS

Chait, From Structure To Signature. 8$^{th}$ Annual SBS Conference & Exhibition, Sep. 22-26, 2002, Netherlands Congress Centre, The Hague, The Netherlands.

Chait, HTS Technology for Analysis of Structural Signatures of Biomolecules: Methodology and Applications. California Separation Science Society, WCBP 2002, 6$^{th}$ Symposium on the Interface of Regulatory and Analytical Sciences for Biotechnology Health Products, Jan. 27-30, 2002.

Durand et al., Protein Glycosylation and Diseases: Blood and Urinary Oligosaccharides as Markers for Diagnosis and Therapeutic Monitoring. Clinical Chemistry. 2000;46(6):795-805.

Everberg et al., Protein pre-fractionation in detergent-polymer aqueous two-phase systems for facilitated proteomic studies of membrane proteins. J Chromatogr A. 2004;1029:113-124.

Fedotoff et al., Influence of Serum Proteins on Conformation of Prostate-Specific Antigen. J. Biomol Struct. Dynamics. Apr. 1, 2012. 29(5): 1051-1064. DOI:10.1080/073911012010525030.

Guiliano, Aqueous Two-Phase Protein Partitioning Using Textile Dyes as Affinity Ligands. Anal. Biochem.1991;197:333-339.

Gulyaeva et al., Relative hydrophobicity of organic compounds measured by partitioning in aqueous two-phase systems. Journal of Chromatograph B.2000;743:187-194.

Guzzetta, Reverse Phase HPLC Basics for LC/MS. An IonSource Tutorial, published Jul. 22, 2001.

Harboe et al., Generation of Antibodies to the Signal Peptide of the MPT83 Lipoprotein of *Mycobacterium tuberculosis*. Scan. J. Immunol. 2002;55:82-87.

Hunger et al., The t(1;19)(q23;p13) results in consistent fusion of E2A and PBX1 coding sequences in acute lymphoblastic leukemias. Blood. 1991;77:687-693.

Kohwi et al., Amphipathic Lipid-Bound Protein Antigens in Mouse Bladder Carcinomas Detected by a Monoclonal Antibody. Biochemistry. 1984;23:5945-5950.

Kuboi, et al., Evaluation of Surface Hydrophobicities of Proteins Using Hydrophobic Interaction with Non-ionic Surfactants in Aqueous Two-Phase Partitioning Systems. Kagaku Kogaku Ronbunshu. 1993;19:446-453.

Labaer et al., So, you want to look for biomarkers (introduction to the special biomarkers issue). J Proteome Res. Jul.-Aug. 2005;4(4):1053-9.

Matsumura et al. A new concept for macromolecular therapeutics in cancer chemotherapy: mechanism of tumoritropic accumulation of proteins and the antitumor Smancs. Cancer Research. 1986;46:6387-92.

Müller et al., Real and Pseudo Oxygen Gradients in Ca-Alginate Beads Monitored During Polarographic Po$_1$-Measurements Using Pt-Needle Microelectrodes. Biotechnology and Bioengineering. 1994;44:617-625.

Peracaula et al., Altered glycosylation pattern allows the distinction between prostate-specific antigen (PSA) from normal and tumor origins. Glycobiology. Jun. 2003;13(6):457-470.

Platt et al., QSAR in grossly underdetermined systems: Opportunities and issues. IBM Journal of Research and Development. 2001;45 (web page).

Richon, A. et al., "An Introduction to QSAR Methodology," (web page; Oct. 1997) Accessed online at http://www.netsci.org/science/compchem/feature19.html.

Sakurai et al., Ligand- and Nuclear Factor-Dependent Change in Hydrophobicity of Thyroid Hormone β$_1$ Receptor. *Thyroid.* 1998;8(4):343-352.

Schena et al., Parallel human genome analysis: Microarray-based expression monitoring of 1000 genes. PNAS. Oct. 1996;93:10614-10619.

Singh et al., Gene expression correlates of clinical prostate cancer behavior. Cancer Cell, 2002;1:203-209.

Sniegoski, An Examination Of The Concentration Of Organic Components Water-Extracted From Petroleum Products. Water Research. 1975;9:421-423.

Stovsky et al., Prostate-specific Antigen/Solvent Interaction Analysis: A Preliminary Evaluation of a New Assay Concept for Detecting Prostate Cancer Using Urinary Samples. Urology. Sep. 2011. 78(3):601-605. Epub Jul. 23, 2011. doi: 10.1016/j.urology.2011.03.071.

Stovsky et al., PSA/SIA: A New Highly Sensitive and Specific Structure-Based Assay for Prostate Cancer (poster), AUA NC 82nd Annual Meeting, Chicago, IL, Sep. 24-27, 2008.

Takano et al. Measuring the Solubility of Liquid Organic Compounds in Water. Journal of the Chemical Society of Japan. 1985, (11):2116-2119.

Takano et al., Solubility Measurement of Liquid Organic Compounds in Water. CAS Online. 1985. 105:60254.

Yan, Detection by ozone-induced chemiluminescence in chromatography. Journal of Chromatography. 1999;842:267-308.

Zaslavsky et al., A New Method for Analysis of Components in a Mixture without Preseparation: Evaluation of the Concentration Ratio and Protein-Protein Interaction. Analytical Biochemistry. 2001;296:262-269.

Zaslavsky, Aqueous Two-Phase Partitioning (Book) Marcel Dekker, New York, Ch. 1-10 (1995).

Zaslavsky, Characteristics of Protein-Aqueous Medium Interactions Measured by Partition in Aqueous Ficoll-Dextran Biphasic System. J. Chromatogr. 1983;260:329-336.

Office Action European Application No. 02795636 dated Feb. 8, 2007.

Office Action European Application No. 02795636 dated Nov. 14, 2005.

Office Action European Application No. 02795636 dated Oct. 27, 2008.

Office Action from Canadian Application No. 2,528,535 dated May 5, 2009.

Office Action from European Application No. 04776693 dated Oct. 10, 2008.

Office Action from European Application No. 04776693 dated Oct. 15, 2007.

Office Action from European Application No. 02768567 dated Mar. 24, 2009.

Office Action European Application No. EP 06851492 dated Mar. 31, 2009.

Office Action from Canadian Application No. 2,466,663 dated Oct. 17, 2011.

Office Action from Canadian Application No. 2,528,535 dated Jul. 23, 2012.

Office Action from Canadian Application No. 2,528,535 dated Nov. 23, 2011.

Office Action from European Application No. 04776693.6 dated Mar. 9, 2012.

Office Action from Australian Application No. 2006345702 dated Jan. 25, 2012.

Office Action from Australian Application No. 2006345702 dated Oct. 10, 2011.

Office Action from Chinese Application No. 200680052677.3 dated Jul. 4, 2012.

Office Action from Chinese Application No. 20068005677.3 dated Oct. 27, 2011.

Office Action from Canadian Application No. 2,466,663 dated May 6, 2010.

Office Action from Canadian Application No. 2,528,535 dated Mar. 15, 2010.

Office Action from U.S. Appl. No. 10/293,959, dated Dec. 5, 2006.
Office Action from U.S. Appl. No. 10/293,959, dated Jun. 29, 2006.
Office Action from U.S. Appl. No. 13/110,345 dated Aug. 5, 2011.
Office Action from U.S. Appl. No. 13/110,345 dated Dec. 6, 2011.
Office Action from U.S. Appl. No. 11/641,611 dated Apr. 5, 2011.
Office Action from U.S. Appl. No. 11/641,611 dated Jan. 5, 2011.
Office Action from U.S. Appl. No. 11/818,911 dated Jun. 23, 2010.
Office Action dated Jul. 13, 2015 for U.S. Appl. No. 14/049,249.
Office Communication dated Jul. 15, 2015 for U.S. Appl. No. 14/049,249.
Office Action from U.S. Appl. No. 10/293,959 dated Jun. 25, 2008.
Office Action from U.S. Appl. No. 10/293,959 dated Apr. 28, 2009.
Office Action from U.S. Appl. No. 10/293,959 dated Jul. 17, 2007.
Office Action from U.S. Appl. No. 10/293,959 dated Jul. 7, 2010.

(56) References Cited

OTHER PUBLICATIONS

Office Action from U.S. Appl. No. 10/779,164 dated Jul. 31, 2009.
Office Action from U.S. Appl. No. 10/779,164 dated Feb. 25, 2010.
Office Action from U.S. Appl. No. 11/641,611 dated Sep. 1, 2010.
Office Action from U.S. Appl. No. 13/316,625 dated Feb. 26, 2013.
Office Action from U.S. Appl. No. 13/316,625 dated Dec. 11, 2012.
U.S. Appl. No. 16/804,313, filed Feb. 28, 2020, Chait et al.

* cited by examiner

SYSTEMS AND METHODS FOR CHARACTERIZATION OF MOLECULES

RELATED APPLICATIONS

This application claims priority to all of the following applications according to the following recitation of priority relationships. This application, is a continuation of U.S. patent application Ser. No. 15/138,538, filed Apr. 26, 2016, entitled "Systems and Methods for Characterization of Molecules," by Chait, et al., which is a continuation of U.S. patent application Ser. No. 14/049,249, filed Oct. 9, 2013, entitled "Systems and Methods for Characterization of Molecules," by Chait, et al., which is a continuation of U.S. patent application Ser. No. 13/316,625, filed Dec. 12, 2011, entitled "Systems and Methods for Characterization of Molecules," by Chait, et al., which is a continuation of U.S. patent application Ser. No. 11/818,911, filed Jun. 15, 2007, entitled "Systems and Methods for Characterization of Molecules," by Chait, et al., which is a continuation-in-part of U.S. patent application Ser. No. 11/440,222, filed May 24, 2006, entitled "Systems and Methods for Characterization of Molecules," by Chait, et al.; which application is a continuation-in-part of U.S. patent application Ser. No. 10/560,373, filed Dec. 12, 2005, entitled "Systems and Methods for Characterization of Molecules," by Chait, et al.; which application claims priority to International Patent Application No. PCT/US04/019343, filed Jun. 14, 2004, entitled "Systems and Methods for Characterization of Molecules," by Chait, et al., published as WO 2004/111655 on Dec. 23, 2004; which application claims priority to U.S. Provisional Patent Application Ser. No. 60/478,645, filed Jun. 12, 2003, entitled "Systems and Methods for Identifying and Using Molecular Markers," by Chait, et al.; and to U.S. Provisional Patent Application Ser. No. 60/561,945, filed Apr. 14, 2004, entitled "Systems and Methods for Characterization of Molecules," by Chait, et al. Each of these applications is incorporated herein by reference.

FIELD OF THE INVENTION

The present invention is generally related to the separation, fractionation, and/or characterization of molecules and/or biomolecules in a mixture. More particularly, the invention is related to developing methods for separation using, for example, aqueous multi-phase partitioning, to discover differences between two or more mixtures of molecules or biomolecules, which can reflect structural and functional characteristics of biomolecules and/or molecules which interact with biomolecules. This invention is also related to discovering, selecting, and using markers for the purpose of classifying mixtures, where the markers are species within the mixture that are different between the mixtures.

BACKGROUND OF THE INVENTION

Many diseases and/or other pathological processes or conditions are caused by dysfunction and/or disregulation of certain proteins. These disease-related proteins may have their structures altered, relative to their "normal" or "wild-type" counterparts and/or may be expressed in larger (up-regulated expression) or lower (down-regulated expression) quantities in a given disease state, relative to "normal" physiological conditions. In some cases, proteins having altered structure and/or function may be used as protein markers associated with a particular human or animal disease, for instance, as a diagnostic for the earlier detection of the disease, or the like. In many cases, the particular protein(s) of relevance to a given pathological process of a disease or other condition are unknown. Identification of such protein(s) would be useful for development of new diagnostic tests, or the like.

One general approach to the identification and characterization of protein markers is based on the analysis of protein compositions of samples of biological material (biological fluids, such as serum, plasma, and cerebrospinal fluid, tissues, cells, etc.) using high resolution separation techniques. For instance, proteins isolated from control and experimental populations can be subjected to proteolytic cleavage, and their cleavage products identified using liquid chromatography (LC) coupled with tandem mass spectrometry (LC-MS-MS). Many protein separation techniques are based on multi-dimensional separation of proteins from a sample, typically by two-dimensional gel electrophoresis (2-DE) or two-dimensional high-performance liquid chromatography (2D-HPLC). The 2-D protein maps may be obtained and compared for pathological samples with those for reference samples; positions of proteins observed as "spots" on 2-DE maps or as "peaks" on 2D-HPLC maps can be compared and those that are present (or absent) in the maps obtained from pathological samples but absent (or present) in the maps obtained from the reference samples may be judged as likely to correspond to pathologically relevant proteins. Additionally, quantities of proteins estimated as intensities of the spots (or peaks) may be evaluated and compared between the pathological and reference samples. Those that are significantly different may be considered as pathologically relevant.

It has also been recently established that a pattern of the presence/absence and/or the relative quantities of multiple proteins (a "signature") may also be of diagnostic relevance, where the proteins judged to be of interest are identified by peptide mapping and mass spectrometry. Mathematical or statistical techniques, such as pattern recognition techniques, could be used to analyze the pattern produced by these experimental techniques and produce a diagnostic classification. However, this approach is often highly inefficient, for example, due to the inherent necessity of analyzing all of the proteins in a given sample, whereas only a small portion of the proteins may have any pathological relevance.

Several different methods for reducing the analytical complexity of protein mixtures have been developed. These methods are typically based on fractionation of the original mixture prior to 2-D analysis by gel electrophoresis or 2-D HPLC. One such method is separation of proteins by the technique of free-flow electrophoresis. However, this technique, while fractionating the original protein mixture, may result in multiple 2-D analysis of simplified fractions, i.e. while reducing the complexity of analysis and improving resolution, it inherently increases the number of samples for further analysis.

Another method is fractionation based on the affinity of proteins to different natural ligands and/or pharmacological compounds; however, this approach, while allowing separation of proteins according to protein functions, may inherently result in an increase in the number of samples for further analysis, and often requires additional knowledge or presumption concerning the differences between the samples.

A disadvantage of most present fractionation techniques is that they generally cannot preserve protein-protein or protein-ligand interactions. Differences among biological interactions are often important for elucidating and detecting changes among samples. Additionally, most of the fractionation techniques today rely on separation due to a fixed physical attribute, such as molecular size or net charge. While these attributes are very important for distinguishing among biomolecules in a complex mixture, they generally do not cover all of the potential differences between biomolecules representing, e.g., normal vs. disease states, differences in configuration etc. Yet another important disadvantage of present fractionation techniques is related to their inability to separate mixtures based on differences between structural changes in, e.g., glycosylation patterns or conformational changes. These changes are often important for identifying proteins that either participate in and/or are the result of a disease state. For example, if a protein is misfolded as a result of genetic mutation, the protein's net charge and size are unlikely to vary significantly, and more importantly, the protein's expression level might be the same for the underlying normal vs. disease states. Finally, natural genetic variability among individuals can significantly contribute to a very large scatter in the expression levels (concentration) of biomolecules in a biological sample. This variability may necessitate the use of statistically large number of samples to robustly detect differences innate to a particular pathological condition rather than to genetic variability. Natural genetic variability often is a significant hindrance in implementing protein marker based diagnostics by reducing sensitivity and/or specificity of the test. A technique that is insensitive to the particular expression level of each biomolecule and instead is sensitive to structural difference in that biomolecule is potentially of great interest in the field.

SUMMARY OF THE INVENTION

The present invention generally relates to the analysis and characterization of biomolecules, complexes comprising biomolecules, molecules which interact with biomolecules and/or analogous species thereof. The results of the analysis can be used to isolate subsets of biomolecules from two or more samples with structural and/or functional properties that are related to differences between such biomolecules, complexes or interacting molecules that underlie the differences among the samples. For example, differences in specific biomolecules may indicate protein markers of a disease and/or physiological state of a living organism.

The subject matter of this application may involve, in some cases, interrelated products, alternative solutions to a particular problem, and/or a plurality of different uses of a single system or article.

Specifically, in one embodiment, the invention involves developing and using methods for fractionation or separation, for example via multi-phase partitioning, of two or more mixtures which may reflect differences between the mixtures related to the structural and/or functional characteristics of one or more molecules and/or molecules which interact with such molecules. These techniques can be used to identify markers in samples, and to techniques to using such markers for diagnostics and other related applications.

In one aspect, the invention relates to a method for identifying one or more tools for physiological analysis. In one embodiment, the method involves determining a relative measure of interaction between prostate specific antigen of a first mixture of species and at least first and second interacting components defining at least a first phase and a second phase, respectively, of a first partitioning system. A relative measure of interaction is also determined between prostate specific antigen of a second mixture of species, and the first partitioning system. A difference is determined in the relative measure of interaction of the prostate specific antigen of the first mixture, versus the prostate specific antigen of the second mixture, with the first system. Based upon this difference, a first system is selected as a tool for determining a physiological condition of a biological system based upon determination of a relative measure of interaction between at least one species of a sample from the biological system and the first system. Alternatively, or in addition, the at least one species of the first mixture and the at least one corresponding species of the second mixture are selected as a marker for determining a physiological condition of a biological system.

In another aspect, the invention involves determining a physiological condition of a biological system. In one embodiment, a method for doing so involves determining a relative measure of interaction between prostate specific antigen arising from a sample from a biological system, and at least first and second interacting components defining at least a first phase and a second phase, respectively, of a first partitioning system. From the process of determining the relative measure of interaction between the first species and the first and second interacting components of the first partitioning system, the physiological condition of the biological system can be determined.

In another embodiment, the method involves determining a physiological condition of a biological system by determining a difference between at least a first marker of a sample from the biological system and a corresponding marker representative of a reference condition of the biological system, without knowledge of the chemical or biological identity of the first marker.

In another embodiment, a method involves determining a physiological condition of a biological system by determining a difference and/or similarity between a first property and/or value of a property associated with a marker obtained from the biological system and from the same marker from at least one sample with at least one reference condition, where the marker was determined by determining a relative measure of interaction between at least one species of a first mixture of species and at least first and second interacting components defining at least a first phase and a second phase, respectively, of a first partitioning system, determining a relative measure of interaction between at least one species of a second mixture of species, corresponding to the first species, and the first system, and defining the at least one species of the first mixture of species and the at least one species of the second mixture of species corresponding to the first species as the marker by denoting a difference between the relative measures of interaction of each of the species with the first partitioning system.

Other advantages and novel features of the invention will become apparent from the following detailed description of various non-limiting embodiments of the invention when considered in conjunction with the accompanying figures. In cases where the present specification and a document incorporated by reference include conflicting disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For the purposes of clarity, not every component is labeled in every figure, nor is every component of each embodiment of the invention shown where illustration is not necessary to allow those of ordinary skill in the art to understand the invention. In the figures.

DETAILED DESCRIPTION

Figure 1:
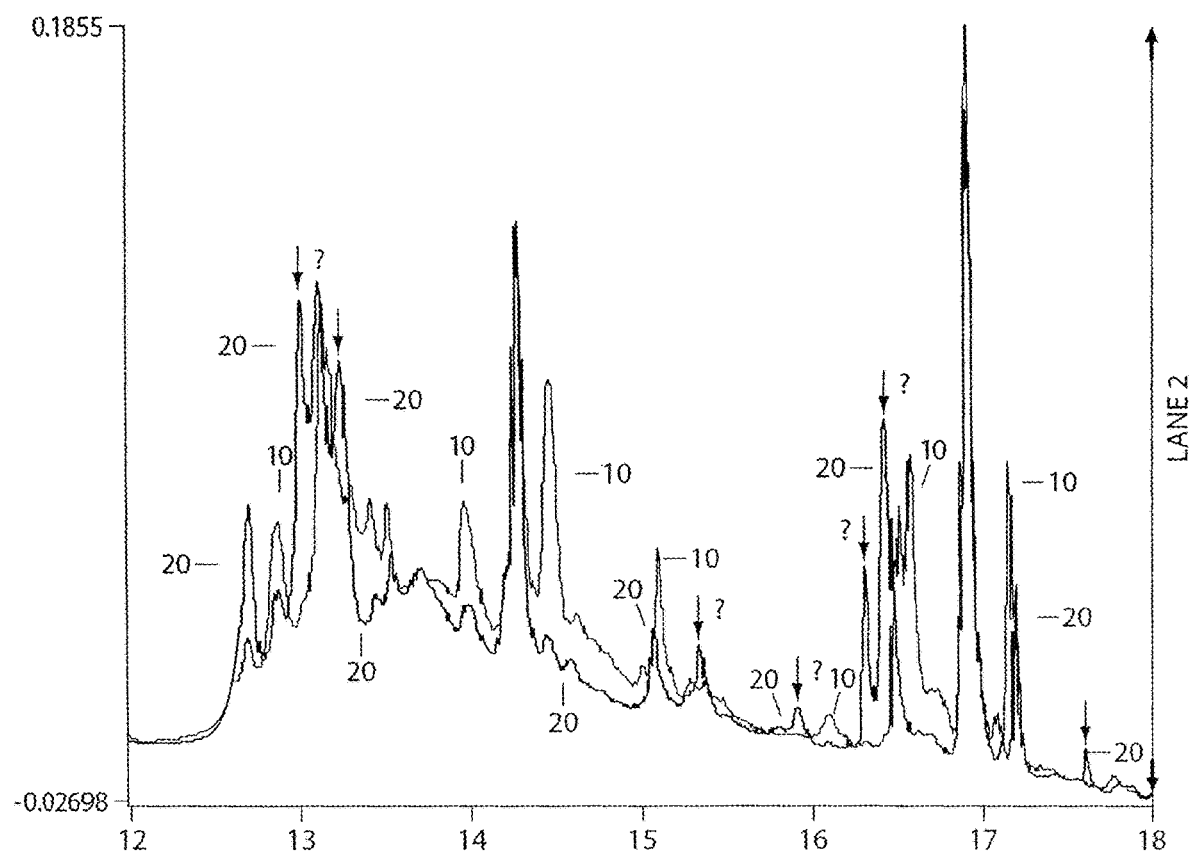
FIG. 1 is a RP-HPLC chromatogram of certain proteins, from a protein mixture, having a 3.5<pI<3.9.

The following documents are incorporated herein by reference in their entirety: U.S. Pat. No. 6,136,960, issued Oct. 24, 2000, entitled "Method for Evaluation of the Ratio of Amounts of Biomolecules or Their Sub-populations in a Mixture," by Chait et al.; U.S. patent application Ser. No. 10/293,959, filed Nov. 12, 2002, entitled "Characterization of Molecules," by A. Chait, et al.; U.S. Patent Application Ser. No. 60/478,645, filed Jun. 13, 2003, entitled "Systems and Methods for Characterization of Molecules," by A. Chait, et al.; U.S. Patent Application Ser. No. 60/561,945, filed Apr. 14, 2004, entitled "Systems and Methods for Characterization of Molecules" by Chait, et al; U.S. patent application Ser. No. 10/560,373, filed Dec. 12, 2005, entitled "Systems and Methods for Characterization of Molecules," by Chait, et al.; and International Patent Application No. PCT/US04/019343, filed Jun. 14, 2004, entitled "Systems and Methods for Characterization of Molecules," by Chait, et al., published as WO 2004/111655 on Dec. 23, 2004.

As used in the specification and the appended claims, the singular forms "a," "an" and "the" include plural referents unless the context clearly dictates otherwise. Thus, for example, reference to "a biomolecule" can include mixtures of a biomolecule, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, "or" is understood to mean inclusively or, i.e., the inclusion of at least one, but including more than one, of a number or list of elements. Only terms clearly indicated to the contrary, such as "exclusively or" or "exactly one of," will refer to the inclusion of exactly one element of a number or list of elements.

"Optional" or "optionally" means that the subsequently described event or circumstance may or may not occur, and that the description includes instances where said event or circumstance occurs and instances where it does not.

"Analyte," "analyte molecule," or "analyte species" refers to a molecule, typically a macromolecule, such as a polynucleotide or polypeptide, whose presence, amount, and/or identity are to be determined.

"Antibody," as used herein, means a polyclonal or monoclonal antibody. Further, the term "antibody" means intact immunoglobulin molecules, chimeric immunoglobulin molecules, or Fab or F(ab')$_2$ fragments. Such antibodies and antibody fragments can be produced by techniques well known in the art, which include, for example, those described in Harlow and Lane (*Antibodies: A Laboratory Manual*, Cold Spring Harbor Laboratory, Cold Spring Harbor, N.Y. (1989)), Kohler et al. (*Nature* 256: 495-97 (1975)), and U.S. Pat. Nos. 5,545,806, 5,569,825 and 5,625,126, each incorporated herein by reference. Correspondingly, antibodies, as defined herein, also include single chain antibodies (ScFv), which may comprise linked $V_H$ and $V_L$ domains and which may retain the conformation and the specific binding activity of the native idiotype of the antibody. Such single chain antibodies are well known in the art and can be produced by standard methods. See, e.g., Alvarez et al., *Hum. Gene Ther.* 8: 229-242 (1997)). The antibodies of the present invention can be of any isotype, for example, IgG, IgA, IgD, IgE and IgM.

"Aqueous," as used herein, refers to the characteristic properties of a solvent/solute system wherein the solvating substance has a predominantly hydrophilic character. Examples of aqueous solvent/solute systems include those where water, or compositions containing water, are the predominant solvent.

"Partitioning system," as used herein, refers to any material having at least two phases, sections, areas, components, or the like, at least two of which can interact differently with at least one species to which they are exposed. For example, a partitioning system can include different areas of a solid surface, which can interact differently with a particular molecule exposed to the different sections, a multi-phase system such as a multi-phase liquid system, e.g., an aqueous/non-aqueous system or an aqueous multi-phase system (defined below) to which one or more species can be exposed and optionally dissolved, at least some of which species can interact differently with different phases. For example, a particular species may have a greater affinity for one phase rather than another phase to the extent that a multi-phase partitioning system can isolate a species from a mixture, or cause a species to partition at least in some way differently between the phases.

"Aqueous multi-phase system," as used herein, refers to an aqueous system which includes greater than one aqueous phase in which an analyte species can reside, and which can be used to characterize the structural state of the analyte species according to the methods described herein. For example, an aqueous multi-phase system can separate at equilibrium into two, three, or more immiscible phases. Aqueous multi-phase systems are known in the art and this phrase, as used herein, is not meant to be inconsistent with accepted meaning in the art. Examples of various aqueous multi-phase systems, and their compositions, are described more fully below.

An "interacting component" means a component, such as a phase of multi-phase system, that can interact with a species and provide information about that species (for example, an affinity for the species). Multiple interacting components, exposed to a species, can define a system that can provide a "relative measure of interaction" between each component and the species. An interacting component can be aqueous or non-aqueous, can be polymeric, organic (e.g. a protein, small molecule, etc.), inorganic (e.g. a salt), or the like, or any combination thereof. A set of interacting components can form a system useful in and in part defining any experimental method which is used to characterize the structural state of a species such as an analyte species according to the methods described herein. Typically, a system of interacting components can measure the relative interaction between the species and at least two interacting components. An aqueous multi-phase system is an example of a system of interacting components, and it is to be understood that where "aqueous system" or "aqueous multi-phase system" is used herein, this is by way of example only, and any suitable system of interacting components can be used.

Where aqueous two-phase and aqueous multi-phase systems are described herein, it is to be understood that other systems, as used herein, systems analogous to those comprising only aqueous solutions or suspensions can be used. For example, an aqueous two-phase system can include non-aqueous components in one or more phases that are not liquid in character. In this aspect, multi-phase systems also refers to related techniques that rely on differential affinity of the biomolecule to one media versus another, wherein the transport of the biomolecule between one medium and, optionally, another medium occurs in an aqueous environment. Examples of such multi-phase systems include, but are not limited to, HPLC columns or systems for liquid-liquid partition chromatography, as are known to those of ordinary skill in the art.

"Relative measure of interaction," with reference to a particular species as used herein, means the degree to which the species interacts with another species or with a phase of a multi-phase system in a relative sense. For example, a particular species may have a greater affinity for one phase of a multi-phase system rather than another phase or phases, the degree to which it interacts with or resides in, that phase as opposed to other phases defines its relative measure of interaction. Relative measures of interaction, in the context of the present invention, are generally determined in a ratiometric manner, rather than an absolute manner. That is, where a species can interact with each phase of a two-phase system but resides more preferably in one than the other, the present invention typically makes use of information as to the ratio of concentration of the species in each of the two phases, but not necessarily of the absolute concentration of the species in either phase. In other cases, the interaction can be an interaction based not upon residence of a particular species within a particular solvent or fluid carrier, but interaction with a solid surface such as a solid phase of a chromatography column where the relative measure manifests itself in elution time, or can involve geometric or spatial interaction such as a particular species interaction with a porous substrate as opposed to that of a different species or a different substrate.

"Partition coefficient," as used herein, refers to the coefficient which is defined by the ratio of chemical activity or the concentrations of a species in two or more phases of a multi-phase system at equilibrium. For example, the partition coefficient (K) of an analyte in a two-phase system can be defined as the ratio of the concentration of analyte in the first phase to that in the second phase. For multi-phase systems, there can be multiple partition coefficients, where each partition coefficient defines the ratio of species in first selected phase and a second selected phase. It will be recognized that the total number of partition coefficients in any multi-phase system will be equal to the total number of phases minus one.

For heterogeneous phase systems, an "apparent partition coefficient," as used herein, refers to a coefficient which describes information obtained from alternative techniques that is correlated to the relative partitioning between phases. For example, if the heterogeneous two-phase system used is an HPLC column, this "apparent partition coefficient" can be the relative retention time for the analyte. It will be recognized by those of ordinary skill in the art that the retention time of an analyte, in such a case, reflects the average partitioning of the analyte between a first, mobile phase and a second, immobile phase. Also, it will be recognized that other, similarly determinable properties of analytes can also be used to quantify differences in physical properties of the analytes (e.g. in other techniques) and are, therefore, suitable for use as apparent partition coefficients.

"Bind," as used herein, means the well-understood receptor/ligand binding, as well as other nonrandom association between a biomolecule and its binding partner. "Specifically bind," as used herein, describes a binding partner or other ligand that does not cross react substantially with any biomolecule other than the biomolecule or biomolecules specified. Generally, molecules which preferentially bind to each other are referred to as a "specific binding pair." Such pairs include, but are not limited to, an antibody and its antigen, a lectin and a carbohydrate which it binds, an enzyme and its substrate, and a hormone and its cellular receptor. As generally used, the terms "receptor" and "ligand" are used to identify a pair of binding molecules. Usually, the term "receptor" is assigned to a member of a specific binding pair, which is of a class of molecules known for its binding activity, e.g., antibodies. The term "receptor" is also preferentially conferred on the member of a pair that is larger in size, e.g., on lectin in the case of the lectin-carbohydrate pair. However, it will be recognized by those of skill in the art that the identification of receptor and ligand is somewhat arbitrary, and the term "ligand" may be used to refer to a molecule which others would call a "receptor." The term "anti-ligand" is sometimes used in place of "receptor."

"Molecule-molecule interaction", such as biomolecule-biomolecule interaction, protein-protein interaction, and the like means an interaction that typically is weaker than "binding," i.e., an interaction based upon hydrogen bonding, van der Waals binding, London forces, and/or other non-covalent interactions that contribute to an affinity of one molecule for another molecule, which affinity can be assisted by structural features such as the ability of one molecule to conform to another molecule or a section of another molecule. Molecule-molecule interactions can involve binding, but need not.

"Biomolecule," as used herein, means a molecule typically derived from an organism, and which typically includes building blocks including nucleotides, and the like. Examples include, but are not limited to, peptides, polypeptides, proteins, protein complexes, nucleotides, oligonucleotides, polynucleotides, nucleic acid complexes, saccharides, oligosaccharides, carbohydrates, lipids, etc., as well as combinations, enantiomers, homologs, analogs, derivatives and/or mimetics thereof.

"Species," as used herein, refers to a molecule or collection of molecules, for example, an inorganic chemical, an organic chemical, a biomolecule, or the like. In the present invention, species generally are biomolecules.

"Corresponding species," as used herein, means at least two different species that are identical chemically or, if they differ chemically and/or by molecular weight, differ only slightly. Examples of corresponding species include structural isoforms of proteins, proteins or other molecules that are essentially identical but that differ in binding affinity with respect to another species or plural species, have different higher-order structure, e.g., differing in secondary or tertiary structure but not differing or not differing significantly in chemical sequence. In general, corresponding species are species that may be arranged differently (isoforms, isomers, etc.) but are composed of the same or essentially the same chemical building blocks.

"Detectable," as used herein, refers the ability of a species and/or a property of the species to be discerned. One example method of rendering a species detectable is to provide further species that bind or interact with the first species, where the species comprise(s) a detectable label. Examples of detectable labels include, but are not limited to, nucleic acid labels, chemically reactive labels, fluorescence labels, enzymic labels and radioactive labels.

"Mimetic," as used herein, includes a chemical compound, an organic molecule, or any other mimetic, the structure of which is based on, or derived from, a binding region of an antibody or antigen. For example, one can model predicted chemical structures to mimic the structure of a binding region, such as a binding loop of a peptide. Such modeling can be performed using standard methods (see, for example, Zhao et al., *Nat. Struct. Biol.* 2: 1131-1137 (1995)). The mimetics identified by methods such as this can be further characterized as having the same binding function as the originally identified molecule of interest, according to the binding assays described herein.

Alternatively, mimetics can also be selected from combinatorial chemical libraries in much the same way that peptides are. See, for example, Ostresh et al., *Proc. Natl. Acad. Sci. U.S.A.* 91: 11138-11142 (1994); Dorner et al., *Bioorg. Med. Chem.* 4: 709-715 (1996); Eichler et al., *Med. Res. Rev.* 15: 481-96 (1995); Blondelle et al., *Biochem. J.* 313: 141-147 (1996); Perez-Paya et al., *J. Biol. Chem.* 271: 4120-6 (1996).

"Solid support," as used herein, means the well understood solid material to which various components of the invention are physically attached, thereby immobilizing the components of the present invention. The term "solid support," as used herein, means a non-liquid substance. A solid support can be, but is not limited to, a membrane, sheet, gel, glass, plastic or metal. Immobilized components of the invention may be associated with a solid support by covalent bonds and/or via non-covalent attractive forces such as hydrogen bond interactions, hydrophobic attractive forces and ionic forces, for example.

"Structure," "structural state," "configuration" or "conformation," as used herein, all refer to the commonly understood meanings of the respective terms, for example, as they apply to biomolecules such as proteins and nucleic acids, as well as pharmacologically active small molecules. In different contexts, the meaning of these terms will vary, as is appreciated by those of skill in the art. The structure or structural state of a molecule refers generally not to the building blocks that define the molecule but the spatial arrangement of these building blocks. The configuration or confirmation typically defines this arrangement. For instance, the use of the terms primary, secondary, tertiary or quaternary, in reference to protein structure, have accepted meanings within the art, which differ in some respects from their meaning when used in reference to nucleic acid structure (see, e.g., Cantor and Schimmel, *Biophysical Chemistry*, Parts I-III). Unless otherwise specified, the meanings of these terms will be those generally accepted by those of skill in the art.

"Physiological conditions," as used herein, means the physical, chemical, or biophysical state of an organism. As most typically used in the context of the present invention, physiological condition refers to a normal (e.g., healthy in the context of a human) or abnormal (e.g., in a diseased state in the context of a human) condition.

"Marker," as used herein, is a species that can be a carrier of information regarding a physiological state of a biological environment within which it resides. A marker can exhibit at least two different properties or values of a specific property or properties (e.g., structural conformation, binding affinity for another species, etc. but not solely different amounts of the species) that correspond to and/or that represent information regarding the two or more physiological states of environments within which they reside. For example, a marker may be a protein that is structurally modified between a first state representative of a healthy system within which it resides and a second structural state (different conformation) representative of a disease system within which it resides.

The state of a molecule, such as a biomolecule, at whatever level of detail, can be affected by many different factors including, but not limited to, changes in the chemical structure of the molecule (e.g., addition, deletion or substitution of amino acids in proteins, covalent modification by chemical agents or cleavage by chemical or thermal degradation, addition or deletion of carbohydrates to the structure, etc.), interactions with one or more other biomolecules or ligands, and the like. Evaluation of different states can be used as one method of determining the potential effectiveness of different molecules, condition of the molecules, condition or state of an environment (e.g., a mixture of species) within which the molecule resides, and the like.

The present invention involves the investigation of the state of molecules. The invention is described in the context of studies involving biomolecules and/or molecules able to interact with biomolecules, but the invention can apply to essentially any molecular species and/or interaction, whether biological, biochemical, chemical, or other species, and those of ordinary skill in the art will understand how the invention can be used in the context of non-biological molecules. It is to be understood that whenever "biomolecules" is used in the description of the invention, any non-biological molecule also can be used or studied.

In one aspect, the present, in some embodiments, invention involves techniques for determining information about the composition of a mixture of biomolecules and/or molecules which interact with biomolecules. The mixture may originate from biological material, such as human clinical sample or other biological fluid, tissue, cells, a subject, etc., or the mixture, may be a synthetic mixture. The mixture can come from a biological system which, as used herein, means a human or non-human mammal, including, but not limited to, a dog, cat, horse, cow, pig, sheep, goat, chicken, primate, rat, and mouse, or a bacteria, virus, fungus, or of plant origin.

The invention also relates to developing and determining characteristics (quantitative and/or qualitative) of a mixture that are obtained, for example, via processing using multiphase partitioning, which can reflect certain structural and functional characteristics of biomolecules or molecules that interact with biomolecules in the original mixture. These characteristics can be used, for example, for establishing relationships between the composition of the mixture and the physiological state of the biological source of the mixture e.g., the state of health or disease of a subject. These characteristics can also be used to design experimental conditions for subsequent fractionation of the mixtures into subsets enriched in the molecule(s) of interest for the purpose of the analysis, while simultaneously reduced in the total number of different molecule(s) in some cases. The systems and methods of the present invention can also be useful for detecting, classifying, and/or predicting changes in a mixture of biomolecules or molecules that interact with biomolecules. For example, the mixture may be a synthetic mixture, or a mixture associated with a particular disease or physiological state of a living organism, cells, tissues, or biological liquids. The systems and methods of the present invention can also be used to detect changes to a predetermined set of biomolecules in a biological mixture and these changes could further be used to detect and classify a diagnostic that is related to such changes.

Examples of such changes in a mixture can be the differences in a property of a species of the mixture, such as its conformation, structure and/or interaction tendency with respect to another molecule or molecules (e.g., its binding affinity or other interaction characteristic with respect to another molecule or molecules). For example, if the mixture includes proteins or other biomolecules, such changes may be induced through primary sequence modification, by degradation of the proteins or other biomolecules through chemical, thermal, or other degradation mechanisms, by interaction with other molecules and/or biomolecules, by interaction with low molecular weight compounds (e.g., hormones, peptides, vitamins, cofactors, etc.), by changes in the relative content or concentration of the constituents of the mixture, by reactions such as enzymatic reactions, etc. The systems and methods of the present invention can be used, in some cases, to detect, analyze and/or characterize biological materials, including but not limited to, polypeptides, proteins, carbohydrates, nucleic acids, polynucleotides, lipids, sterols, and mixtures or derivatives thereof, e.g., for the purpose of detection of, or onset of, a particular disease or physiological state, monitoring its progress, treatment, etc.

Comparison and classification steps involved in the invention can make use of additional information not necessarily related to (not directly derived from) the analytical methods of the invention. For example, blood pressure, temperature, blood glucose level, and/or essentially any other measurable physiological condition can be used in conjunction with techniques of the invention to analyze one or more physiological conditions.

As mentioned, multiple partitioning steps can take place so that additional information and/or sensitivity can be obtained. For example, prior to determining relative measures of interaction of each species in each of two or more different mixtures, and following partitioning of both mixtures in two or more partitioning systems of identical (or nearly identical) composition, a quantity of the first and/or the second interacting components of both systems containing the mixtures can be further introduced into a second set of two identical systems with at least two interacting components. Then, partitioning of both second sets of systems for both mixtures takes place, and relative measures of interaction for each species in each mixture can be determined. The species that differ among the mixtures by differences in their relative measures of interaction can be denoted. Then, optionally, a set of one or more species that partition differently can be further selected as a set of markers that are subsequently used to classify additional mixtures as similar to either the first or second mixtures. Determining steps can be performed separately for each species in connection with the set of markers, or simultaneously. Species-specific probes can be used, such as antibodies. Comparison or classification steps to determine markers and use such markers can involve the use of mathematical or statistical techniques known to those of ordinary skill in the art.

It will be recognized by those of ordinary skill in the art that these biological materials can be found in any suitable form, for example, in the form of extracts from natural sources, biological liquids, collections of molecules generated by combinatorial chemical or biochemical techniques and combinations thereof, synthetically created, etc.

In one embodiment, the present invention provides a method to determine certain conditions under which variations among samples representing different compositions (or mixtures of species) could be detected, i.e., determining a set of criteria and/or system components as a "tool," or a part of a tool, to determine information. For example, the ability of a system to determine a relative measure of interaction between a species and one or more interacting components that can define one or more phases of the system can serve as an important tool or component of such a tool. Specifically, as one example, the partitioning of the constituents of a sample between two phases having different chemical or biochemical affinities or other characteristics, such as solvent structures, may separate the constituents by their relative affinity for media of different properties or composition. This separation technique thus can include or, alternatively, can be unlike those typically used in proteomics or similar techniques, e.g., 2-D gel electrophoresis, in which charge and size differences are the two dimensions used to separate the constituents of a sample. In some cases, e.g., for many applications in proteomics, the present invention provides the ability for performing sequential or serial partitioning, with either the same of different conditions, which may result in additional amplification of differences in the fractionated samples. These fractions may be further analyzed using standard proteomics techniques.

As mentioned elsewhere herein, aqueous multi-phase (e.g., two-phase) partitioning systems are well-suited for use in many or most embodiments of the invention, but other partitioning systems can be used. Where "aqueous two-phase partitioning" or "aqueous multi-phase partitioning" is used, it is to be understood that other systems can be used. Partitioning of a biopolymer in aqueous two-phase systems may depend on its three-dimensional structure, type and topography of chemical groups exposed to the solvent, etc. Changes in the 3-D structure of a receptor induced by some effect, e.g., by binding of a ligand binding or by structural degradation, also can change the topography of solvent accessible chemical groups in the biomolecule, or both the topography and the type of the groups accessible to solvent. One result of these changes may be an alteration in the partition behavior of the biomolecule and/or the ligand-bound receptor.

In some cases, the level of concentration of biomolecules in biological samples is strongly dependent upon genotyping. Thus, identification of differences in biomolecules attributable to diseased verses normal states may necessitate using a statistically significant number of samples to negate the effect of natural genetic variations in many cases. In the present invention, in many cases, the effect of genetic variability leading to under- or overexpression can be separated from differences to biomolecules that are traced to their diseased versus normal states. This separation can be achieved by subjecting a sample or other mixture of species containing biomolecules or other molecules to partitioning in one or more different systems, and determining a relative measure of interaction between at least one species in the sample/mixture with various components of the system(s).

This can be done, for example, by separating, using conventional techniques, the two interacting components of each sample, calculating the partition coefficient for each species in the diseased and normal samples, and selecting the species exhibiting different partition coefficients for further analysis and identification. As specific examples, the relative measure of interaction can involve fractionating at least a portion of the first portion and second portion (and/or more portions) of the system. This fractionating can involve electrophoresis such as one-dimensional electrophoresis, two-dimensional electrophoresis, can involve liquid or other chromatography, can involve performing mass spectrometry on at least a portion of the first, second (and, alternately, more portions) of the system, etc. Different partition coefficients typically are not related to the absolute level of expression of each species, but instead, may be related to changes to the structure, binding to other molecules or other changes of relevance to their biological effects, etc. Thus, the present invention provides, in one set of embodiments, means for the identification of changes to biomolecules in a biological mixture inherent to their function and not their absolute level, without necessarily requiring a large statistical number of samples to negate the effect of individual variability in the expression levels.

Once the biomolecules of interest are identified using the above technique, a subset can be selected providing acceptable sensitivity/specificity diagnostics levels for an underlying physiological condition, e.g., a disease. Rapid and specific quantification techniques are readily available to those of ordinary skill in the art which can be used to quantify the concentration of each of the biomolecules in the subset using standard methods and techniques directly in the biological sample, e.g., using antibodies in an Enzyme Linked ImmunoSorbent Assay (ELISA). The concentrations in the two interacting components of each system can be used to calculate the values of the partition coefficients. Changes to the individual values of the partition coefficients thus may indicate certain changes to the biomolecules. In some cases, the change to the partition coefficient of a single biomolecule can result in a definitive diagnostics. In other cases, the use of a pattern of partition coefficient values (a "signature") can be used to enhance the specificity of the method. In yet other cases, partitioning of the samples in multiple systems and performing the steps above, then observing the pattern of values for one or more biomolecules, can provide an alternative way to constructing a sensitive and specific diagnostics method.

Similarly, such changes may be detected using other systems and methods which have an underlying dependence upon the topography and/or the types of solvent accessible groups. Examples of such other methods include, but are not limited to, column liquid-liquid partition chromatography (LLPC), a heterogeneous two-phase system, or a multiphase heterogeneous system. In some cases, an apparent partition coefficient may be generated that expresses the relative changes in the average partitioning between a first and a second phase. For example, in LLPC, the retention volume of a receptor may be used as the apparent partition coefficient.

Aqueous two-phase systems are well-known to those of ordinary skill in the art, and can arise in aqueous mixtures of different water-soluble polymers or a single polymer and a specific salt. When two or more certain polymers, e.g., dextran ("Dex") and polyethylene glycol ("PEG"), or one or more certain polymers and one or more inorganic salts, e.g. polyvinylpyrrolidone ("PVP") and sodium sulfate, are mixed in water above certain concentrations, the mixture can separate into two (or more) immiscible aqueous phases under certain conditions. There is a discrete interfacial boundary separating any two phases, for example, such that one is rich in one polymer and the other phase is rich in the other polymer or the inorganic salt. The aqueous solvent in one or both phases may provide a medium suitable for biological products. Two-phase systems can also be generalized to multiple phase system by using different chemical components, and aqueous systems with a dozen or more phases are known in the art and can be used in connection with the invention.

When a species is introduced into such a two-phase system, it may distribute between the two phases. In this and other systems, the species can be found at different concentrations within each phase, or can be at the same concentration within each phase. Partitioning of a solute can be characterized by the partition coefficient "K," defined as the ratio between the concentrations of the solute the two immiscible phases at equilibrium. It has previously been shown that phase separation in aqueous polymer systems may result from different effects of two polymers (or a single polymer and a salt) on the water structure (B. Zavlavsky, *Aqueous Two-Phase Partitioning: Physical Chemistry and Bioanalytical Applications*, Marcel Dekker, New York, 1995). As the result of the different effects on water structure, the solvent features of aqueous media in the coexisting phases can differ from one another. The difference between phases may be demonstrated by techniques such as dielectric, solvatochromic, potentiometric, and/or partition measurements.

The basic rules of solute partitioning in aqueous two-phase systems have been shown to be similar to those in water-organic solvent systems (which can also be used as systems in the present invention). However, what differences do exist in the properties of the two phases in aqueous polymer systems are often very small, relative to those observed in water-organic solvent systems, as would be expected for a pair of solvents of the same (aqueous) nature. The small differences between the solvent features of the phases in aqueous two-phase or multi-phase systems can be modified so as to amplify the observed partitioning that results when certain structural features are present.

It is known that the polymer and salt compositions of each of the phases usually depend upon the total polymer and/or salt composition of an aqueous two-phase system. The polymer and/or salt composition of a given phase, in turn, usually governs the solvent features of the aqueous media in this phase. These features include, but are not limited to, dielectric properties, solvent polarity, ability of the solvent to participate in hydrophobic hydration interactions with a solute, ability of the solvent to participate in electrostatic interactions with a solute, and hydrogen bond acidity and basicity of the solvent. All these and other solvent features of aqueous media in the coexisting phases may be manipulated by selection of polymer and salt composition of an aqueous two-phase system. These solvent features of the media may govern the sensitivity of a given aqueous two-phase system toward a particular type of solvent accessible chemical groups in the receptor. This sensitivity, type, and topography of the solvent accessible groups in two different proteins, for example, can determine the possibility of separating proteins in a given aqueous two-phase system.

In some cases, a particularly sensitive system may be required, i.e., a system that is very sensitive to, and able to determine relative measures of interaction with respect to, two very similar species. This sensitivity may be of importance when, for example, subtle differences are being detected between the conformational changes in a receptor induced by binding of closely related chemical compounds. The present invention provides efficient and successful systems and methods for screening aqueous phase compositions to identify and/or amplify differences between the compositions of two mixtures. By utilizing a wide variety of different conditions to screen each molecule, as described herein, different partitioning behavior may be obtained reliably without the need to fully understand the underlying theory of aqueous two-phase partitioning, or any of the other related or substitutable techniques.

Biomolecules such as proteins, nucleic acids, etc. may be distributed between the two or more phases when placed into such a system. For example, in the case where phase-forming polymers are used, solutions comprising one or more of the two polymers and the biomolecule may be mixed together such that both phase-forming polymers and the biomolecule are mixed. The resulting solution is resolved and a two-phase system is formed. Optionally, centrifugation can be used to enhance separation of the phases. It will be recognized by those of ordinary skill in the art that partitioning behavior of a biomolecule may be influenced by many variables, such as the pH, the polymers used, the salts used, factors relating to the composition of the system, as well as other factors such as temperature, volume, etc. Optimization of these factors for desired effects can be accomplished by routine practice by those of ordinary skill in the relevant arts, in combination with the current disclosure.

Evaluation of data from partitioning of a biomolecule can involve use of the partition coefficient, in some embodiments of the invention. For example, the partition coefficient of a protein can be taken as the ratio of the protein in first phase to that in the second phase in a biphasic system. When multiple phase systems are formed, there can be multiple independent partition coefficients, each of which can be defined between any two phases. It will be recognized that the partition coefficient for a given biomolecule of a given conformation will be a constant if the conditions and the composition of the two-phase system to which it is subjected remain constant. Thus, if changes are observed in the partition coefficient for a protein upon addition of a potential binding partner, these changes can be presumed to result from changes in the protein structure caused by formation of a protein-binding partner complex. The partition coefficient K, as used herein, is a specifically mathematically defined quantity as further described below, and the term includes coefficients representing the relative measure of interaction between a species and at least two interacting components. It should also be recognized that differences between partition coefficients of corresponding species in two or more mixtures could indicate, in addition to potential structural changes, also binding or lack of binding of such species to other species in the mixtures.

In a non-limiting example of one partitioning system, aqueous multiphase systems are known to be formable from a variety of substances. For example, in order to determine the partition coefficient of a protein (or a mixture of a protein with another compound) to be analyzed, concentrated stock solutions of all the components (polymer 1, e.g., dextran; polymer 2, e.g., PEG, polyvinylpyrrolidone, salts, etc.) in water can be prepared separately. The stock solutions of phase polymers, salts, and the protein mixture can be mixed in the amounts and conditions (e.g., pH from about 3.0 to about 9.0, temperature from about 4° C. to 60° C., salt concentration from 0.001 to 5 mol/kg) appropriate to bring the system to the desired composition and vigorously shaken. The system can then be allowed to equilibrate (resolve the phases). Equilibration can be accomplished by allowing the solution to remain undisturbed, or it can be accelerated by centrifugation, e.g., for 2-30 minutes at about 1000 g to 4000 g, or higher. Aliquots of each settled (resolved) phase can be withdrawn from the upper and/or lower phases (or from one or more phases, if multiple phases are present). The concentration of molecule(s) can be determined for each phase.

Different assay methods may be used to determine the relative measures of interaction between species and interacting components, e.g. in the form of the concentration of the biomolecules in each phase of a multi-phase system. The assays will often depend upon the identity and type of biomolecule present. Examples of suitable assay techniques include, but are not limited to, spectroscopic, immunochemical, chemical, fluorescent, radiological and enzymatic assays. When the biomolecule is a peptide or protein, the common peptide or protein detection techniques can be used. These include, but are not limited to, direct spectrophotometry (e.g., monitoring the absorbance at 280 nanometers) and dye binding reactions with Coomassie Blue G-250 or fluorescamine, o-phthaldialdehyde, or other dyes and/or reagents. Alternatively, if the protein is either an antibody or an antigen, certain immunochemical assays can be used in some cases.

The concentration of the biomolecule(s) in each phase can be used to determine the partition coefficient of the sample under the particular system conditions. Since the partition coefficient reflects the ratio of the two concentrations, the absolute values are not typically required. It will be recognized that this can allow certain analytical procedures to be simplified, e.g., calibration can be eliminated in some instances. It also may have significant advantage for negating the effect of natural variability in the absolute concentration of proteins in samples obtained from, e.g., biological systems, when comparing two or more samples, thus focusing on those changes detected as differences in the partition coefficient relevant to changes to the structure of the individual species in the samples.

It should be recognized by those skilled in the art that the steps in above description of obtaining the partition coefficient could be substituted by other steps or measurements. Depending on the size, volumes, amount of the biomolecule, detection system, discrete or continuous operation using either liquid-liquid or liquid-solid portioning, other processes that effectively result in results described herein could be developed. Such modifications and different processes should not limit the scope of this complete invention.

The partition coefficient can then be compared with other partition coefficients. For example, a partition coefficient for a species can be compared to the partition coefficients for the species under different conditions, a partition coefficient for a species can be compared to the partition coefficients for the species when combined with other species, a set of partition coefficients for a species can be compared to other sets of partition coefficients, etc. This comparative information can be obtained at the same time or near the same time and in the same system or a similar system as is used to determine the interaction characteristics of the molecules of interest, or can be provided as pre-prepared data in the form of charts, tables, or electronically stored information (available on the internet, disc, etc.)

In one embodiment of the present invention, proteins or other biomolecular mixtures from an experimental sample and from a reference sample (determined simultaneously, previously, or subsequently, as described above) may be caused to partition in a variety of different aqueous two-phase systems, e.g. formed by different types of polymers, such as Dextran and PEG or Dextran and Ficoll, by the same types of polymers with different molecular weights, such as Dextran-70 and PEG-600 or Dextran-70 and PEG-8,000, by the same polymers but containing different in type and/or concentration salt additives, different buffers of different pH and concentration, etc. The overall partition coefficients for the mixtures determined using a particular assay procedure (e.g., same for both samples) can be determined in all of the systems. In one embodiment, the systems displaying different partition coefficients for the mixtures under comparison may be selected as a separation medium, for example, for further fractionation and/or characterization of the mixtures. In another embodiment, mixtures are partitioned using one or more standard systems with known properties, e.g., those providing enhanced sensitivity levels towards hydrophobic or ionic interactions. In such a case, the individual partition coefficients of the species comprising the mixtures may be determined following separation of the mixtures in the phases and/or compared between two or more mixtures.

The reasons for the observed differences in the partition behavior of the two samples do not have to be scientifically characterized for such differences to be useful for many applications, e.g., for diagnostics. Such differences, resulting in partitioning behavior, may arise due to multiple reasons, including relative compositional, structural, or conformational differences in the samples when exposed to aqueous media of different solvent structures.

In one set of embodiments, the systems and methods proposed herein provide techniques for the separation and fractionation of proteins while preserving complexes and biomolecular interactions that may be of interest to distinguishing among samples. The solvent media in aqueous partitioning may be selected to be compatible with the mixture of biomolecules. The solvent media may also be selected to preserve the higher-order structures, as well as non-covalent binding among biomolecules such as proteins, small molecular weight ligands, etc. For example, appearance or disappearance of complexes by the methods of this invention can be useful for diagnostics and other applications.

One aspect of the present invention provides systems and methods able to distinguish among different samples, without being rigidly tied to few separation dimensions or variables, such as charge and/or size. One non-limiting example application of the present invention is to provide an adjustable separation dimension, in which changes to individual species can be uncovered via determination of their individual partition coefficients, enabling detection and identification of changes that can not be detected using conventional separation means, such as molecular size or charge.

In one embodiment, the present invention can be used to discover one of more biomolecules in a biological sample, which is changed between normal and diseased state of the underlying organism. In this case, a set of typically multiple systems, each known to provide sensitivity to structural changes leading to differences in their hydrophobic, ionic, etc. interactions with the interacting components, can be tested with the same samples. One or more species can be identified as markers in one or more systems using techniques described herein. This marker or markers can subsequently be used for diagnostics applications.

In yet another embodiment, the set of markers and the associated systems in which such markers were discovered can be used during diagnostics screening. In this case, the diagnostics test can include one or more of the following steps which can be carried out in any order suitable for such screening: (1) Partitioning the sample in one or more of the systems which were used during the marker discovery study; (2) Measuring the marker(s) concentration(s) using specific assay using, e.g., antibodies, in each of the interacting components of the systems; (3) Calculating the partition coefficients for each individual biomarker in one or more systems; (4) Comparing the values to those representing normal and diseased states which were obtained during the marker discovery study using any combination of statistical or mathematical techniques; and (5) Denoting a diagnostics based on such a comparison.

Without a loss of generality, as an example, searching for a biomarker or a set of biomarkers (e.g., to increase clinical specificity) denoting a disease can involve one or more of the following steps, again, carried out in any suitable order:

1. Prepare one or more aqueous two-phase partitioning systems.
2. Add samples of plasma (homogenized tissue, urine, saliva, etc.) corresponding to normal and diseased state origins.
3. Partition the samples in the aqueous two-phase systems.
4. Remove aliquots from both phases of the aqueous two-phase systems for each sample. After this step there will be two aliquots for each sample.
5. Perform additional separation steps (e.g., 2D gel electrophoresis or 2D HPLC) to separate the proteins in each aliquot.
6. Quantitate each protein in each aliquot.
7. Calculate the individual partition coefficient for each protein in each set of aliquots corresponding to the same sample.
8 Compare the partition coefficients for each protein (e.g., in the same spot on the charge/size map on a gel) for the normal vs. diseased states.
9. Select one or more proteins (even without knowing their identity) as potential biomarker by their different values of the partition coefficients for the two types of samples.
10. Optionally perform additional identification steps such as LC-MS/MS. It should be noted that discovering and selecting the marker(s) in the present invention does not require the steps of protein identification.

It should also be noted that the marker is comprised in the present invention of the species selected in the manner described above, and another important tool in the process can involve the specific composition of the aqueous two-phase partitioning system or other system that can be used to determine relative measures of interaction. It should be recognized that multiple partitioning systems of different compositions can be used in the above procedure. The final selection of a set of markers most useful for subsequent diagnostics depends typically on a trade off among the competing attributes of the increase in specificity and cost when additional biomarkers are included in the final set.

Once a set of biomarkers is discovered using the above protocol, a diagnostics screening test can be devised, without a loss of generality, according in the following manner:

Upon a preliminary step performed once during the preparation of the screening test, an appropriate protein-specific concentration assay is developed for each of the proteins in the biomarker set (typically antibodies). Typically once a biomarker is determined using a particular partitioning system, aliquots of the separated biomarker can be used to study its properties and sequence, and antibodies developed for subsequent quantitation of the biomarker directly in complex mixtures using, e.g., ELISA.

Then, the screening test is comprised of the following, again, in any suitable order:

1. Obtain a sample of plasma (homogenized tissue, urine, saliva, etc.) corresponding to unknown state (normal or diseased).
2. Add aliquots of the sample to the partitioning system used during the discovery of the biomarkers. If more than one system was used, repeat the same step for each different partitioning system.
3. Perform partitioning of the sample in each of the systems.
4. Use the protein specific assay for each protein to quantitate the concentration of each of the proteins in the biomarkers set, in each of the two phases of each partitioning system.
5. Calculate the partition coefficient for each of the proteins in the biomarkers set.
6. Compare, using appropriate statistical or other techniques the partition coefficients from the sample of unknown origin to those corresponding to the normal and diseased states.
7. Classify the unknown sample as diagnostically similar to one of the known samples.

In another embodiment, a screening test can be accomplished without requiring partitioning as described above. Once a biomarker is discovered and selected using techniques described herein, it typically refers to a protein that is structurally different in the two samples (e.g., diseased vs. normal). Once the protein is isolated, identified using standard techniques such as LC-MS/MS, and its sequence denoted, a separate procedure can be invoked in some cases to design and raise antibodies that directly differentiate between the two forms of the protein that define the marker. These so-called multi-site antibodies can be used in lieu of the partitioning step in the screening procedure, e.g., as follows, in any suitable order:

1. Obtain a sample of plasma (homogenized tissue, urine, saliva, etc.) corresponding to unknown state (normal or diseased).
2. Directly test the sample with antibody specific to one form of the marker.
3. Classify the unknown samples as diagnostically similar to one of the known samples.

In the protocol described above, the use of form-specific antibody to replace the use of partitioning to delineate different forms of the biomarker may be only possible once the biomarker is discovered using techniques described herein.

It is also noted that the present invention carries the same benefit for the more general and practical case in which the biomarker represents a mixture of forms of the same protein. In such a case, changes in the distribution or relative amounts of the different forms of the same protein will result in a different partitioning behavior of the biomarker, which will be detected using techniques described herein. Therefore the use of the term "biomarker" in the present invention may denote either a single molecule that with different forms between the two samples, or mixtures of two or more forms of the same molecule that differ in the relative amounts of the forms between the two samples.

In connection with all aspects of the invention, a variety of studies can take place, both at the level of determining tools for physiological analysis and carrying out physiological analysis itself. For example, tools for determining analysis procedures can involve taking samples from a single individual or multiple individuals. In one embodiment, a positive sample and a control sample can be taken from a single individual. For example, an individual may have a tumor and a positive sample may be a portion of the tumor, where a control sample is from a non-tumorous portion of the individual. The samples, both positive and control, can be taken from the individual at the same time or at different times. For example, samples from a tumorous portion of an organism can be taken at different times, and used to determine differences in at least one species in each of the samples as tools for analysis of the progression of a tumor.

Similarly, single species or multiple species can be used as markers. Multiple species from a single sample can be identified as separate markers for a particular condition, and during analysis separate species can be studied. As one example, a single species can define a marker identified by or studied in connection with a single partitioning system. In another embodiment, multiple species from a single sample can be identified as separate markers for a particular condition, and during analysis separate species can be studied. Alternatively or in addition, multiple partitioning systems can be used to study behavior of a single species versus its corresponding species (markers). Or, multiple species can be studied and/or identified as markers in a single system or multiple species can be identified and/or studied in connection with multiple partitioning systems.

According to one aspect of the present invention, a computer and/or an automated system is provided able to automatically and/or repetitively perform any of the methods described herein. As used herein, "automated" devices refer to devices that are able to operate without human direction, i.e., an automated device can perform a function during a period of time after any human has finished taking any action to promote the function, e.g. by entering instructions into a computer. Typically, automated equipment can perform repetitive functions after this point in time. One specific example of a technique that can make use of a computer or other automated system is in a process in which a physiological condition of a system as determined by determining a relative measure of interaction between one or more species from a sample from the system and various interacting components of a partitioning system. In the clinical setting, this may be accomplished by drawing a sample of blood (milliliter-sized or a very small sample such as a drop or less) and subjecting the blood sample or a subset thereof (e.g., plasma) to a multi-phase partitioning process. The results of this process can then be compared to similar behavior of markers in a similar system, which can take the form of data stored electronically.

Figure 3:
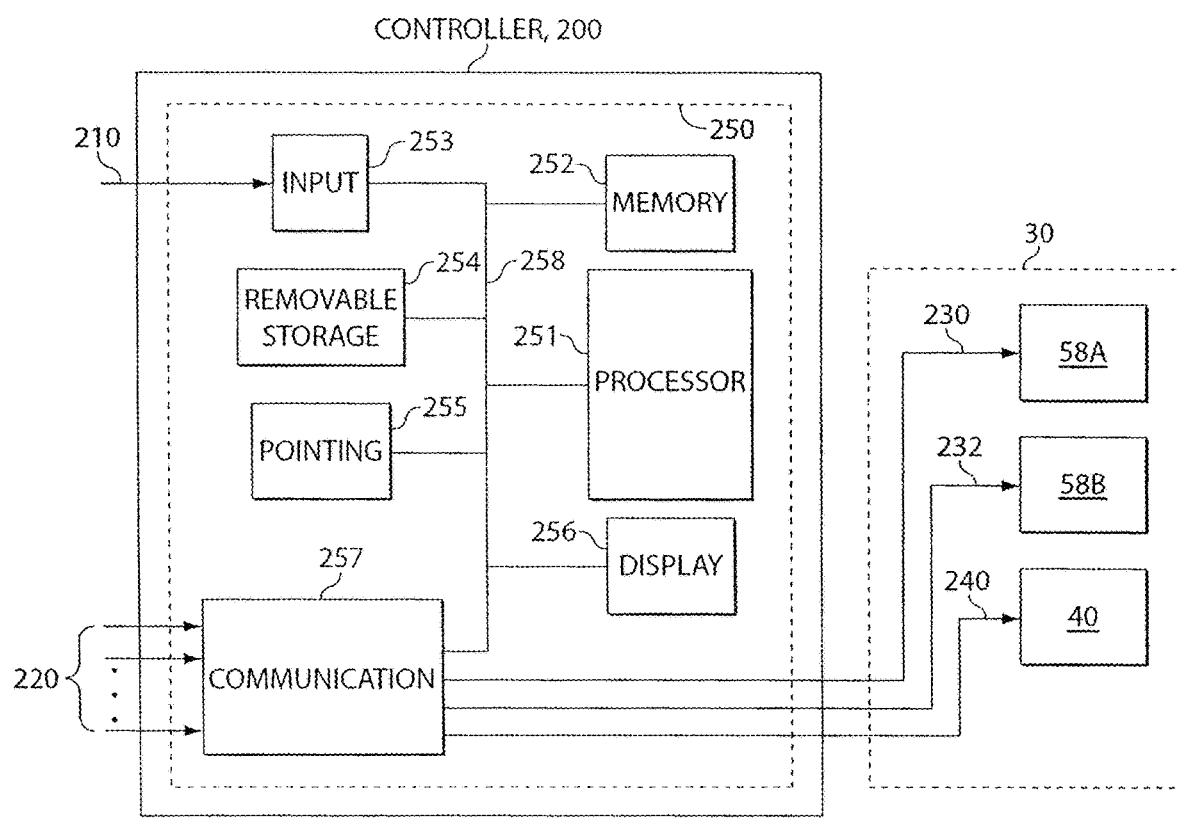
FIG. 3 is a schematic block diagram of a controller according to one embodiment of the present invention.

FIG. 3 is a schematic block diagram of an example system according to one embodiment of the present invention. In the embodiment illustrated in FIG. 3, a controller 200 is implemented on a conventional personal computer 250 that includes a processor 251, a memory 252, an input device 253, optionally a removable storage device 254, a pointing device 255, a display device 256, and a communication device 257, all coupled together via a bus 258. In a conventional manner, memory 252 may include a variety of memory devices, such as hard disk drives or optical disk drives, RAM, ROM, or other memory devices and combinations thereof, and input device 253 may include a keyboard, a microphone, or any other form of input device capable of receiving one or more inputs 210 from a user of controller 200. Removable storage device 254 may include a CD-ROM drive, a tape drive, a diskette drive, etc. and may be used to load application software, including software to implement various embodiments of the present invention described herein. Display 256 may include a conventional CRT display screen, a flat panel display screen, or any other type of display device that allows textual information to be displayed to the user, and pointing device 255 may include a puck, a joystick, a trackball, a mouse, or any other type of pointing device or scrolling device that permits the user to select from among the various textual information displayed on the display device 256. Communication device 257 may include any form of communication transceiver capable of receiving one or more inputs 220 from the fluid-handling apparatus 30 and providing one or more outputs to the fluid-handling apparatus 30. For example, communication device 257 may include a RS232/485 communication transceiver, a 4-20 mA analog transceiver, an Ethernet transceiver, etc.

Software, including code that implements embodiments of the present invention, may be stored on some type of removable storage media such as a CD-ROM, tape, or diskette, or other computer readable medium appropriate for the implemented memory 252 and the removable storage device 254. The software can be copied to a permanent form of storage media on the computer 250 (e.g., a hard disk) to preserve the removable storage media for back-up purposes. It should be appreciated that in use, the software is generally and at least partially stored in RAM, and is executed on the processor 251.

Various embodiments of the present invention can also be implemented exclusively in hardware, or in a combination of software and hardware. For example, in one embodiment, rather than a conventional personal computer, a Programmable Logic Controller (PLC) is used. As known to those skilled in the art, PLCs are frequently used in a variety of process control applications where the expense of a general purpose computer is unnecessary. PLCs may be configured in a known manner to execute one or a variety of control programs, and are capable of receiving inputs from a user or another device and/or providing outputs to a user or another device, in a manner similar to that of a personal computer. Accordingly, although embodiments of the present invention are described in terms of a general purpose computer, it should be appreciated that the use of a general purpose computer is exemplary only, as other configurations may be used.

As shown in FIG. 3, the controller 200 is adapted to be coupled to a fluid handling apparatus 30, to control operation of the fluid handling apparatus. Controller 200 includes an input 210 to receive one or more parameters from a user of the controller 200 relating to the desired operation to be performed. The controller 200 also includes a plurality of inputs 220 to receive signals relating to the operational status of the fluid handling apparatus, and a plurality of outputs 230, 240 to configure and control the fluid handling apparatus. User input parameters received on input 210 may include the type and amount of protein and/or other biomolecules that is to be processed by the fluid handling apparatus, the compositions of liquids used by the fluid handling apparatus for, e.g., liquid-liquid partitioning, etc.

Some embodiments of the present invention permit the user to specify one or a number of input parameters relating to the operation of the fluid handling apparatus, and then, based upon the input parameters, to configure and control the fluid handling apparatus. Depending upon the number of input parameters specified by the user, the controller may prompt the user for additional parameters prior to configuring the fluid handling apparatus.

Inputs 220 of controller 200 are adapted to receive a plurality of signals relating to the operational status of the fluid handling apparatus. Signals that may be received on inputs 220 generally correspond to physical conditions within the fluid handling apparatus, and may include, for example, the concentration of proteins or other molecules within the fluid handling apparatus, the time of exposure, the time for settling to occur, the degree of agitation, the operating temperature or pressure, etc.

Outputs 230, 240 of the controller 200 are adapted to configure and control the fluid handling apparatus, based upon the user parameters received at input 210, and optionally, one or more of the signals received on inputs 220. Output 230 may provide a number of separate signals, for example, a signal to introduce a protein or other molecule within a liquid, a signal to control the operating temperature, etc.

According to another embodiment of the present invention, controller 200 may include a database and/or a knowledgebase that can be accessed by processor 251. According to one embodiment of the present invention, the database may include a plurality of records, each record corresponding to a particular set of parameters for which the fluid processing apparatus may be used to determine a relative measure of interaction. Unless specifically indicated otherwise, as used hereinafter, the term "parameters" is used to refer to both process parameters (e.g., the amount of protein or other biomolecule(s) to be added, the operating temperature etc.), as well as characteristics (e.g., concentration, separation time, etc.) of the experiment given a particular set of process parameters. In general, each of the records stored in the database reflects empirical data based upon use of the fluid processing apparatus under defined conditions, or the use of a similar fluid processing apparatus under defined conditions. The controller 200 and the database may thus be viewed as forming an "expert" system. The database may be stored on a removable storage medium and copied to memory 252 for use by the processor 251, or alternatively, the controller may be pre-configured to include the database.

As will be described further below, the database (or knowledgebase) may be configured for a particular type of fluid handling apparatus (e.g., a specific model from a particular manufacturer of fluid handling apparatus), or may be configured to be used with a variety of types of fluid handling apparatuses. In some cases, the database may be configured for a particular type of protein and/or other biomolecule. Alternatively, a more general database may be used that includes a number of different proteins, biomolecules, aqueous solutions, etc. with which a variety of different fluid handling apparatuses may be used. In use, the database may be accessed by a fluid handling apparatus configuration and control routine that is performed by controller 200 to configure and control fluid handling apparatus 30 that is operatively coupled thereto. It should be appreciated that while the database or knowledgebase is initially based on empirical data obtained with similar equipment, the database may be periodically updated (e.g., new records may be added and/or existing records may be modified) to reflect additional data obtained in use, or by use of similar equipment.

The techniques and apparatus described herein can be used to discover markers or to execute a diagnostics test, in some aspects of the invention. The apparatus could be interfaced to other devices and instruments known to those skilled in the art, including automated sample preparation instruments, automated immunoanalyzers, etc. Data obtained from such devices and instruments could be electronically channeled to a software for performing data reduction and analysis and for delineating a diagnostics.

The following examples are set forth so as to provide those of ordinary skill in the art with a complete disclosure and description of examples of how the compounds, compositions, articles, devices and/or methods claimed herein are made and evaluated, and are intended to be purely exemplary of the invention, and are not intended to limit the scope of what is to be regarded as the complete invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The following examples are intended to illustrate certain aspects of certain embodiments of the present invention, but do not exemplify the full scope of the invention.

Example 1

In this example, it was demonstrated that partitioning of a mixture can be used to or assist in revealing structural changes in proteins.

Human serum albumin (fatty acid and gamma-globulins free), concanavalin A, cytochrome c from horse heart, beta-lactoglobulin A from bovine milk, beta-lactoglobulin B from bovine milk, ribonuclease B from bovine pancrease, lysozyme from chicken egg white, o-phthaldialdehyde reagent (complete), and Bradford Reagent were purchased from Sigma Chemical Company (St. Louis, Mo., USA) and used without further purification. A stock solution of a mixture of 25.6 mg albumin, 12.9 mg concanavalin A, 8.2 mg cytochrome c, 12.2 mg ribonuclease B, 8.4 mg of beta-lactoglobulin A, and 11.5 mg beta-lactoglobulin B was prepared by dissolving in 40 ml of water. Lysozyme in the amount of 2.1 mg was dissolved in 8 ml of this stock solution. Relative measures of interaction of species in these mixtures were determined by subjecting these protein solutions to partitioning in a series of different aqueous two-phase systems as indicated below.

One aqueous two-phase system contained 12.16 wt % Dextran-69 (molecular weight of about 69,000), 6.05 wt % PEG-6000 (molecular weight of about 6,000), 0.43 M $NaClO_4$, and 0.01 M sodium phosphate buffer (pH 7.4). Each system was prepared by mixing the appropriate amounts of stock polymer, salt, and buffer solutions dispensed by liquid handling workstation Hamilton ML-2200 into a 1.2 mL microtube. A total volume of 740 microliters was dispensed to the microtube. A varied amount (0, 24, 48, 72, 96, and 120 microliters) of the protein stock solution or that of the lysozyme solution in the protein stock solution and the corresponding amount (120, 96, 72, 48, 24, and 0.0 microliters) of water were added to a system. The ratio between the volumes of the two phases of each system of a final volume of 1.00 mL was as 1:1. The system was shaken vigorously and then centrifuged for 30 min at about 1700 rpm to speed resolution of the two phases. Tubes were then taken from the centrifuge, aliquots of a given volume (20 microliters for fluorescence-based assay analysis and 10 microliters for Bradford assay analysis) from the top and the bottom phases were withdrawn in duplicate. Each aliquot was diluted, mixed with appropriate reagents, and used for the concentration analysis as described below.

The total protein concentrations in each phase were assayed by measuring the relative fluorescence intensity in wells of a 96-well microplate with a fluorescence microplate reader Bio-Tek F-6000 using an excitation filter at 360 nm and an emission filter at 460 nm. For this purpose, aliquots of 20 microliters from the top and the bottom phases were withdrawn, each mixed with 50 microliters water and 250 microliters o-phthaldialdehyde reagent, and placed into wells of a microplate for fluorescence measurements. The measured fluorescence intensities of the aliquots from the top phases were plotted as a function of the fluorescence intensities of the aliquots from the bottom phases. The partition coefficient for a given protein mixture was determined as a slope of the linear curve representing the plot.

In addition, the protein concentrations in each phase were assayed by measuring the optical absorbance at 595 nm with a using a Spectramax Plus[384] (Molecular Probes) UV-VIS spectrophotometer reader. For this purpose aliquots of 10 microliters from the top and the bottom phases were withdrawn, each mixed with 50 microliters water and 260 microliters Bradford Reagent and placed into wells of a microplate for optical absorbance measurements. The mixtures were shaken for 15 min at 37° C., and the optical absorbance at 595 nm was measured in each well. The optical absorbance at 595 nm of the aliquots from the top phases were plotted as a function of the optical absorbance at 595 nm of the aliquots from the bottom phases (individual data not shown). The partition coefficient for the protein was determined as a slope of the linear curve representing the plot.

The partition experiments were carried out in duplicate. The overall partition coefficient values determined with two different assays agreed within 2-3% error range in each case. The individual partition coefficients of each protein in the mixture were determined in separate experiments performed with individual proteins and are shown in Table 1.

TABLE 1

| Protein Composition | K-Value for individual protein Mixture A* | K-Value for individual protein Mixture B |
| --- | --- | --- |
| Albumin | 2.60 | 2.60 |
| Concanavalin A | 0.33 | 0.33 |
| Cytochrome c | 0.04 | 0.04 |
| Hemoglobin | 4.27 | 4.27 |
| beta-Lactoglobulin A | 0.25 | 0.25 |
| beta-Lactoglobulin B | 0.32 | 0.32 |
| Lysozyme | 6.74 | 6.74 |
| Ribonuclease (A or B) | 2.93 | 0.95 |

Typically, these partition coefficients would not be available a priori. Rather, partitioning of the entire mixture in the aqueous two-phase system would result in partitioning of individual proteins according to their structural details. Following the mixture partitioning, standard separation techniques, such as two-dimensional electrophoresis, could be used to quantify the concentrations of each individual protein in the top and bottom phases of the aqueous system for each of the mixtures. The partition coefficients of each separated species can then be calculated from its concentration values in the top and bottom phases and results similar to Table 1 would be obtained. However, separation of the mixtures based on size and charge alone using standard proteomics techniques would not have shown variations since the total concentration of each species did not change in the two mixtures. Instead, in this case, only the structure of a single protein was altered (in this case, glycosylation pattern).

This example thus illustrates that structural changes to individual proteins are detectable, even if their concentrations remained the same in the various mixtures. Using one or more partitioning systems that offer sensitivity towards different structural variations, followed by total mixture partitioning and standard separation techniques and determination and comparison of the individual partition coefficients, can be used to reveal changes to proteins that are not possible with conventional separation techniques. Furthermore, these changes could readily be detected and used for diagnostics screening using techniques described herein.

Example 2

In this example, it was demonstrated that the overall partition coefficients of total human plasma proteins from patients with a particular disorder, as compared to healthy donors, are different under particular partition conditions, and that this can serve as a basis for determination of physiological conditions of biological systems. It was also demonstrated that these conditions may be used for fractionation of the plasma for further analysis of the plasma fractions by a standard proteomics approach. The overall procedure can then be used for discovery of particular proteins differing in amount and/or structure in the original samples. These proteins can also subsequently be used as markers specific to the disorder. This example does not intend to provide definite data and does not define a definite procedure for discovering markers that underlie the particular clinical condition described; rather, it should serve as an illustrative example only.

Human plasma samples were obtained from several patients with posttraumatic stress disorder (used as experimental samples) and from several people with the similar combat experience but without posttraumatic stress disorder (used as reference samples). One sample from each set (experimental and reference) was selected at random, and used for screening experiments as described below. Portions of the samples were diluted ca. 30-fold with water, and subjected to partitioning in a variety of aqueous two-phase systems. Several systems were found to display the different overall distribution of total plasma proteins from the samples under comparison.

One aqueous two-phase system (PEG-$Na_2SO_4$) contained 15.70 wt % PEG-600 (molecular weight of about 600), 9.47 wt % $Na_2SO_4$, and 2.30 wt % sodium/potassium phosphate buffer (pH 7.4). Each system was prepared by mixing the appropriate amounts of stock polymer, salt, and buffer solutions dispensed by liquid handling workstation Hamilton ML-2200 into a 1.2 mL microtube. A total volume of 670 microliters was dispensed to the microtube. A varied amount (0, 30, 60, 90, 120, and 150 microliters) of the diluted plasma sample and the corresponding amount (190, 160, 130, 100, 70, and 40.0 microliters) of water were added to a system. The ratio between the volumes of the two phases of each system of a final volume of 0.86 mL was as 1:1. The system was shaken vigorously and then centrifuged for 30 min at about 1700 rpm to speed resolution of the two phases. Tubes were then taken from the centrifuge, and aliquots of a fixed volume from the top and the bottom phases were withdrawn in duplicate.

The protein concentrations in each phase were assayed by measuring the optical absorbance at 595 nm using a Spectramax Plus[384] (Molecular Probes) UV-VIS spectrophotometer reader. For this purpose, aliquots of 10 microliters from the top and the bottom phases were withdrawn, each mixed with 50 microliters water and 260 microliters Bradford Reagent and placed into wells of a microplate for optical absorbance measurements. The mixtures were shaken for 15 min at 37° C., and the optical absorbance at 595 nm was measured in each well. The optical absorbance at 595 nm of the aliquots from the top phases were plotted as a function of the optical absorbance at 595 nm of the aliquots from the bottom phases (individual data not shown). The partition coefficient for the protein was determined as a slope of the linear curve representing the plot.

Another aqueous two-phase system (Dex-PEG) contained 11.32 wt % Dextran-69 (molecular weight of about 69,000), 14.57 wt % PEG-600 (molecular weight of about 600), and 0.14 M sodium phosphate buffer (pH 7.4). Each system was prepared by mixing the appropriate amounts of stock polymer, salt, and buffer solutions dispensed by liquid handling workstation Hamilton ML-2200 into a 1.2 mL microtube. A total volume of 620 microliters was dispensed to the microtube. A varied amount (0, 30, 60, 90, 120, and 150 microliters) of the diluted plasma sample and the corresponding amount (180, 150, 120, 90, 60, and 30.0 microliters) of water were added to a system. The ratio between the volumes of the two phases of each system of a final volume of 0.80 mL was as 1:1. The system was shaken vigorously and then centrifuged for 30 min at about 1700 rpm to speed resolution of the two phases. Tubes were then taken from the centrifuge, and aliquots of a fixed volume from the top and the bottom phases were withdrawn in duplicate.

The protein concentrations in each phase were assayed by measuring the optical absorbance at 595 nm using a Spectramax Plus[384] (Molecular Probes) UV-VIS spectrophotometer reader. For this purpose, aliquots of 10 microliters from the top and the bottom phases were withdrawn, each mixed with 50 microliters water and 260 microliters Bradford Reagent and placed into wells of a microplate for optical absorbance measurements. The mixtures were shaken for 15 min at 37° C., and the optical absorbance at 595 nm was measured in each well. The optical absorbance at 595 nm values of the aliquots from the top phases were plotted as a function of the optical absorbance at 595 nm values of the aliquots from the bottom phases. The partition coefficient for the protein was determined as a slope of the linear curve representing the plot.

The results of analysis of overall distribution of total plasma proteins in the two indicated systems are presented in Table 2, which shows the overall partition coefficients of total plasma proteins from four patients with posttraumatic stress disorder (PTSD, represented by the four rows under that heading for each of the two systems) and three healthy donors, represented by the three rows under that heading for each of the two systems, in aqueous two-phase systems.

TABLE 2

| | Overall Partition Coefficient, $K_p$ | |
| --- | --- | --- |
| System | Patients with PTSD | Healthy donors |
| PEG-$Na_2SO_4$ | 4.16 ± 0.05 | 3.03 ± 0.07 |
| | 4.42 ± 0.10 | 3.62 ± 0.05 |
| | 3.92 ± 0.09 | 2.79 ± 0.08 |
| | 3.98 ± 0.13 | |
| Dex-PEG | 2.93 ± 0.05 | 2.74 ± 0.06 |
| | 3.54 ± 0.06 | 2.99 ± 0.08 |
| | 3.41 ± 0.05 | 3.05 ± 0.05 |
| | 3.02 ± 0.08 | |

The data presented in Table 2 thus indicate that the overall distribution of total plasma proteins differs between the samples from patients with posttraumatic stress disorder and samples from healthy donors in the aqueous PEG-$Na_2SO_4$ two-phase system to a larger extent than in the aqueous Dex-PEG two-phase system. Therefore, the former system was used for fractionation of the samples by extraction.

Aqueous PEG-Na$_2$SO$_4$ mixtures of total final system volume 4.0 ml each were prepared. Plasma samples (undiluted) of 0.3 ml volume each were added to the mixtures, vortexed, and centrifuged as described above. Following settling of the phases, aliquots of about 1.5 ml volume were withdrawn from the upper phases and 2-D HPLC analysis of the extracts was performed. The 2-D HPLC analysis included two separation steps. The first step was chromatofocusing separation was performed using the HPCF 1D column (Eprogen, Darien, Ill.) with a flow rate of 0.2 ml/min, a buffer gradient from pH 8.5 to pH 4.0 and detection at 280 nm. The pH of the eluate was monitored and the fractions of proteins within certain pH ranges are collected. The fractions collected from the first dimension HPLC separation were then analyzed in the second dimension by reversed-phase HPLC (RP-HPLC). Reversed-phase HPLC separation was performed using a nonporous HPRP-2D column (Eprogen, Darien, Ill.) at 50° C. with flow rate of 0.75 ml/min, acetonitrile gradient from 0 to 100% in 30 min and detection at 214 nm. The injection volume of each fraction obtained in the first procedure was 500 microliters.

Figure 2:
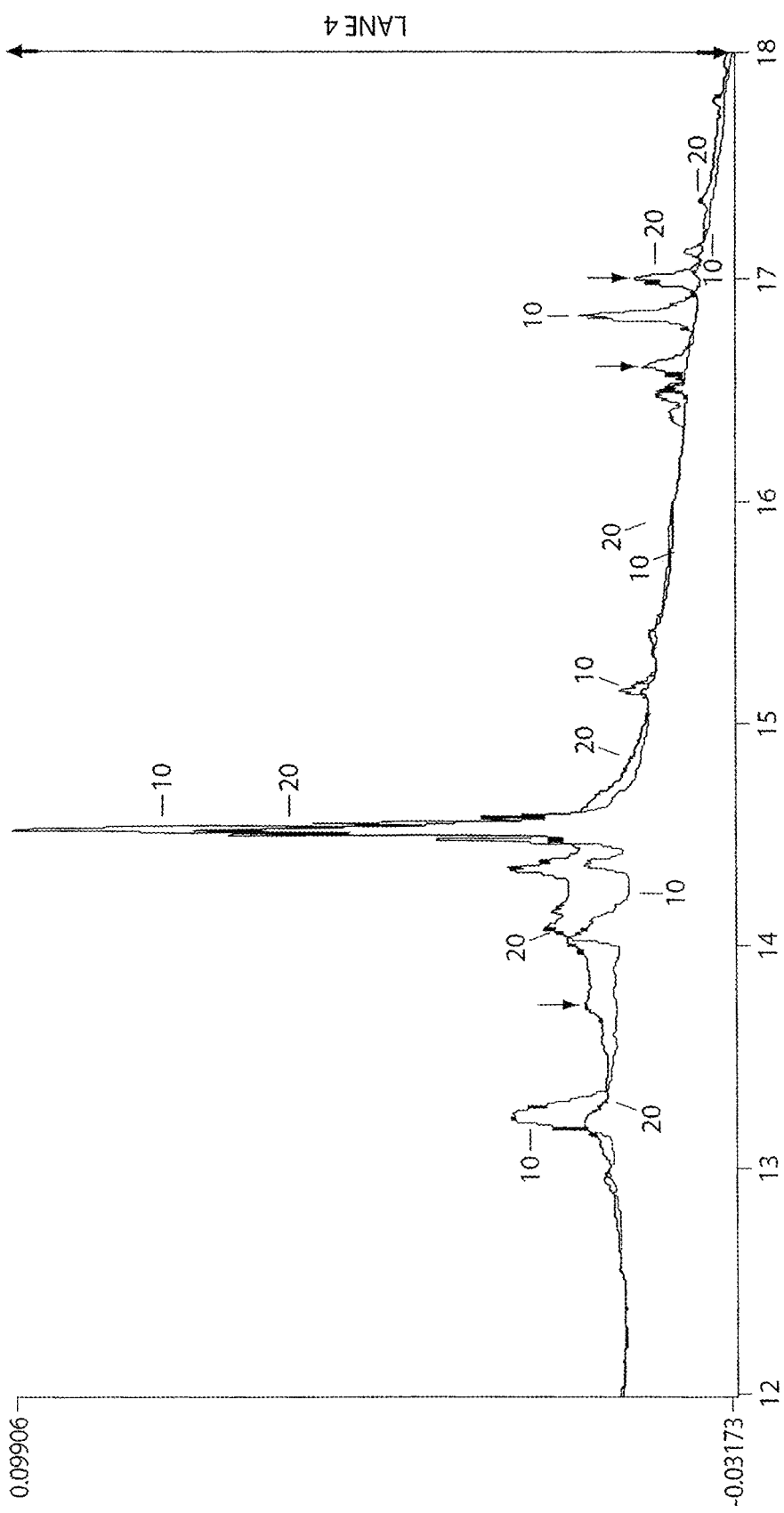
FIG. 2 is a RP-HPLC chromatogram of certain proteins, from the same protein mixture as FIG. 1, having a 4.3<pI<4.6.

The typical results of the 2-D HPLC analysis are presented in FIGS. 1 and 2. FIG. 1 shows the RP-HPLC chromatogram of proteins selected from the above samples that had a pI range of 3.5<pI<3.9. The chromatogram of the extract from control plasma sample is indicated as 10; the chromatogram of the extract from the PTSD sample is indicated as 20. The peaks in the PTSD sample with retention times that were different from those observed in the control plasma sample are denoted with arrows with question marks in FIG. 1. Peaks which appeared in the PTSD sample but were absent from the control sample are denoted by arrows. FIG. 2 shows a similar RP-HPLC chromatogram analysis of selected proteins having a pI from 4.3 to 4.6. All the marks as indicated with respect to FIG. 1.

These results illustrate that the protein patterns of extracts from the samples under comparison were found to be different. These differences according to the chromatograms shown in FIGS. 1-2 include different relative amounts of the proteins (displayed as different relative heights of the peaks on chromatograms), different structures of the proteins (displayed as different retention times or positions of the peaks on chromatograms), and the appearance and/or lack of certain proteins in the samples under comparison (displayed as appearance/disappearance of peaks on chromatograms).

As a hypothetical (prophetic) section of this example, a more definitive study for discovering markers under the procedures described herein can include performing the same 2-D HPLC assays on the other phases of the partitioning systems, to be followed by calculation of the individual partition coefficients of each peak. Differences between coefficients corresponding to each peak in the two cases of healthy vs. positive then define each peak as a potential marker. The marker can then be used for subsequent diagnostics of unknown samples in the manner described herein.

This demonstrates the ability of the invention to be effective even without determining the chemical or biological identity of specific species that are analyzed in (e.g., via study of relative measures of interaction) and used in connection with the invention.

Thus, this example illustrates that the analysis of the overall protein distribution in a particular aqueous two-phase system displayed different distribution behavior of total plasma proteins from blood of patients with a certain disease and from blood of healthy donors. It was found that there were different overall distributions of total plasma proteins from the samples under comparison. As described above, further analysis of the fractions by proteomics analysis can also be performed, and further analysis and calculation of the individual partition coefficients of certain peaks of interest that are different between the samples could be performed and used for diagnostics screening as described by the present invention. Alternatively, site-specific antibodies could be developed against proteins that underlie certain peaks showing differences, thus bypassing the need for partitioning in the screening stage of such markers.

Example 3

In this example, it was demonstrated that relative measures of interaction, exemplified herein as the partition coefficients of aqueous two-phase partitioning systems, of certain human serum proteins from patients with a particular physiological condition, were different than those corresponding to healthy donors, and that such differences could serve as a basis for determination of physiological conditions of biological systems. Selection of partitioning conditions suitable for discovering changes in the structure of certain proteins, and/or in their interactions with other proteins in serum, was also illustrated. Furthermore, this example illustrates one method of identifying particular proteins as potential biomarkers from a group of proteins in biological fluids using methods described in the present invention.

Serum samples from patients diagnosed with early stage ovarian cancer and healthy women were obtained from Gynecologic Oncology Group (GOG, Columbus, Ohio). The 250 microliters aliquots of sera from each of 10 patients with ovarian cancer were combined and mixed, and used as a pool. The 250 ul microliter aliquots of sera from 10 healthy women were also combined and mixed, and used as a pool. Portions of 75 microliters volume from each pooled sample were subjected to partitioning in a variety of 24 aqueous two-phase systems.

Each aqueous partitioning system was prepared by mixing the appropriate amounts of stock polymer, salt, and buffer solutions dispensed by liquid handling workstation Hamilton ML-4000 into a 1.2 mL microtube. For example, one aqueous two-phase system (Dex-Ficoll) contained 18.00 wt % Ficoll-70 (molecular weight of about 70,000), 13.00 wt % Dextran-75 (molecular weight of about 75,000), 1.00 wt % sodium chloride, and 0.01 M sodium/potassium phosphate buffer (pH 7.4). A total volume of 500 microliters was dispensed to the microtube. A fixed amount of 75 microliters of pooled serum sample and 75 microliters of water were added to a system. The ratio between the volumes of the two phases of each system of a final volume of 0.65 mL was as 1:1. The system was shaken vigorously and then centrifuged for 60 min at about 1700 rpm to speed resolution of the two phases. Tubes were then removed from the centrifuge, and aliquots of a fixed 100 microliters volume from the top and the bottom phases were withdrawn. Each aliquot was diluted 5-fold with water and stored at −80° C. The same procedure was followed with both serum samples from pooled sample of sera from patients with ovarian cancer and from pooled sample of sera from healthy women. The same protocol was also used for partitioning in all of the different aqueous two-phase systems screened.

The frozen diluted aliquots from top and bottom phase of each aqueous two-phase system used for screening were coded and shipped to Luminex Core Facility at Hillman Cancer Center (Pittsburgh, Pa.), where standard LabMap assays (Bio-Rad Laboratories, Hercules, Calif.) were utilized for measuring concentrations of certain proteins, such as interleukin (IL)-8, vascular endothelial growth factor VEGF, basic fibroblast growth factor (bFGF), tumor necrosis factor alpha (TNF-alpha), tumor necrosis factor receptor (TNF-R1), granulocyte colony-stimulating factor (G-CSF), and others. The LabMap assays were performed in 96-well microplate format according to appropriate manufacturer's protocols. Samples were analyzed using the Bio-Plex suspension array system (Bio-Rad Laboratories, Hercules, Calif.) as described in the literature. See, for example, Gorelik et al., *Cancer Epidimiol. Biomarkers Prev.*, 14(4), 981-987 (2005). Analysis of experimental data was performed using five-parametric-curve fitting.

The partition coefficient for each individual protein in each aqueous two-phase system was calculated as the ratio of the protein concentration assayed in the top phase to that in the bottom phase. The concentrations of 65 proteins out of about 80 different proteins which assayed in both phases of 24 different aqueous two-phase systems could not be reliably assayed in one or both phases of at least some of aqueous two-phase partitioning systems. In other cases, the partition coefficient could be determined, for example, for pooled serum from ovarian cancer patients but not for serum from healthy women. These cases were eliminated from further consideration.

In many cases, individual serum proteins the partition coefficients were determined to be statistically indistinguishable, within the concentration assay error margin, between sera samples from cancer patients and healthy women. Such cases denote either of the following interpretations: (1) there were no structural changes for the particular protein under consideration between normal and cancer samples; (2) the particular aqueous partitioning system was not suitable for identifying structural changes in the particular protein under examination. In the former case, the protein could be rejected as a potential marker, while in the latter case the partitioning system could be rejected as being unsuitable for discerning differences in the specific protein. Thus the combination of protein and system could be rejected for denoting a difference in a physiological condition between the samples.

For a number of individual proteins, however, it was possible to establish the partition conditions under which the changes in the protein structure and/or protein interactions with other proteins were observed between the cancer and normal sera samples as significant differences between the partition coefficient values, K, for a given protein. The results obtained for several protein markers and partition conditions used are presented in Table 3.

TABLE 3

| Partitioning System* | Protein** | K (serum from healthy women) | K (serum from cancer patients) |
|---|---|---|---|
| A | EGFR | 5.11 | 6.94 |
| H | | 0.39 | 0.68 |
| A | IL-8 | 5.35 | 4.14 |
| G | | 7.05 | 4.18 |
| D | | 5.60 | 4.34 |
| E | G-CSF | 0.68 | 0.15 |
| F | | 1.06 | 1.63 |
| B | | 0.75 | 0.24 |
| C | | 0.29 | 0.02 |
| B | sIL-6R | 1.92 | 1.05 |
| A | IGFBP-1 | 5.13 | 3.93 |

TABLE 3-continued

| Partitioning System* | Protein** | K (serum from healthy women) | K (serum from cancer patients) |
|---|---|---|---|
| A | bFGF | 0.41 | 1.04 |
| A | RANTES | 3.34 | 1.97 |

*Partitioning Systems: A: 18.0 wt % Ficoll-70, 13.0 wt % Dextran-75, 2.2 wt % K/Na phosphate buffer, pH 7.4; B: 8.0 wt % Ficoll-70, 13.0 wt % Dextran-75, 1 wt % NaCl, 0.15 wt % K/Na phosphate buffer, pH 7.4; C: 18.0 wt % Ficoll-70, 13.0 wt % Dextran-75, 3.8 wt % NaCl, 0.15 wt % K/Na phosphate buffer, pH 7.4; D: 15.7 wt % PEG-600, 1.0 wt % NaCl, 18.1 wt % K/Na phosphate buffer, pH 7.4; E: 15.7 wt % PEG-600, 9.5 wt % $Na_2SO_4$, 1.0 wt % NaCl, 0.64 wt % K/Na phosphate buffer, pH 7.4; F: 15.7 wt % PEG-600, 9.5 wt % $Na_2SO_4$, 4.8 wt % NaCl, 0.64 wt % K/Na phosphate buffer, pH 7.4; G: 15.7 wt % PEG-600, 9.5 wt % $Na_2SO_4$, 3.8 wt % NaCl, 2.3 wt % K/Na phosphate buffer, pH 7.4; H: 15.7 wt % PEG-600, 9.5 wt % $Na_2SO_4$, 1.0 wt % NaCl, 2.3 wt % K/Na phosphate buffer, pH 7.4;
**Proteins: EGFR: epidermal growth factor receptor; IL-8: interleukin-8; G-CSF: granulocyte colony-stimulating factor; sIL-6R: soluble interleukin-6 receptor; IGFBP-1: insulin-like growth factor binding protein 1; bFGF: basic fibroblast growth factor; RANTES: beta-chemokine (regulated upon activation, normal T-cell expressed and secreted).

This example demonstrates certain aspects, including the following: (1) partitioning systems may be selected or rejected as tools to determine changes in physiological conditions; (2) individual proteins may be selected or rejected as potential markers for same application; (3) specific combinations of protein and systems may be used individually or in tandem to screen individuals for changes in physiological conditions. Screening of individuals using biomarkers discovered according to some methods described in the present invention may be accomplished after at least one combination of a partitioning system and a protein are designated as suitable for establishing differences in physiological conditions of clinical relevance. Such screening could be accomplished, using the present example, in several principal manners (additional ways may be defined by those skilled in the art). One manner relies on using a single protein and a single system, e.g., EGFR with system A, or EGFR with system H, or IL-8 with system G. Actual clinical use of a single protein and system as a biomarker suitable for diagnosing a particular disease may involve further procedures to establish its sensitivity and specificity using techniques known to those skilled in the art. Another manner relies on using a single partitioning system and multiple proteins. For example, a clinical diagnostic assay may comprise serum partitioning in a single aqueous two-phase system followed by immunoassay analysis of several individual proteins of clinical value, for example, system A in Table 3, for analysis of changes in partition coefficients for, e.g., EGFR, IL-8, IGFBP-1, bFGF, and RANTES. This manner might be especially useful since it requires a single partitioning step of serum, followed by a multiplexed immunoassay. The use of multiple protein markers for diagnosis can increase the sensitivity and specificity trade-off and is recognized by those skilled in the art. Yet another manner in which screening may be efficiently accomplished is using different systems and proteins to arrive at a desired statistical performance parameters. For example, different aqueous two-phase systems could be used for analysis of changes in partition coefficients of different individual proteins, e.g., system H for EGFR, system G for IL-8, system E for GT-CSF, system B for sIL-6R, system A for bFGF, RANTES, and IGFBP-1, etc. Still another manner may involve using several aqueous two-phase systems for analysis of partition coefficients of a single protein.

Example 4

This example illustrates that partitioning of prostate specific antigen (PSA) in urine may be independent of the total PSA concentration in urine and serum.

Urine samples were collected from patients who were candidates for prostate biopsy based on serum PSA levels above 4 ng/ml, or based on other clinical presentations, such as pelvic pain and voiding disfunction or other physiological abnormalities. The urine samples were collected immediately post prostate massage, a clinical protocol performed by a physician, and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use. Urine samples from 9 patients with prostate cancer as established by prostate biopsy analysis were thawed and combined to form a "cancer" urine pool sample. Urine samples from patients established to be free of prostate cancer according to results from prostate biopsy analysis were thawed and combined to form a "control" urine pool sample. These pool samples were stored at −80° C. until further use.

Dextran-75 (with molecular weight of 60,000 to 90,000) was purchased from USB Corporation (Cleveland, Ohio, USA) and used without further purification. Ficoll-70 (with molecular weight of about 70,000) was purchased from GE Healthcare Bio-Sciences Corp. (Piscataway, N.J., USA) and used without further purification. All inorganic salts of ACS reagent grade were purchased from Sigma Chemical Company (St. Louis, Mo., USA) and used without further purification. Stock solutions of individual polymers and inorganic salts in water were prepared gravimetrically and used to form aqueous two-phase system as described below.

The aqueous two-phase system contained 18.00 wt % Ficoll-70, 13.00 wt % dextran-75, and 0.15 M NaCl in 0.010 M sodium/potassium phosphate buffer (pH 7.4). Each system was prepared by mixing the appropriate amounts of stock polymer, salt and buffer solutions by weight into a 1.2 mL microtube up to a total weight of a system of 0.426 g (volume 0.369 mL) using a MICROLAB 4000 MPH-4 liquid handling robotics workstation (Hamilton Company, Reno, Nev., USA). Urine samples from individual patients in amounts of 0.075 mL were added to each system. The systems were vigorously shaken by vortexing and centrifuged for 60 min at about 2500 rpm in a refrigerated centrifuge set to room temperature and equipped with a microplate rotor to speed the phase settling. The microtubes were taken out of the centrifuge, and aliquots of 100 microliter from the top and the bottom phases were withdrawn and each diluted with 0.400 ml water for PSA concentration analysis.

PSA concentration was determined in each aliquot by an automated enzyme-linked immunosorbent assay (ELISA), Elecsys Total PSA Immunoassay with a lower detection limit of 0.002 ng/ml (Roche Diagnostics, Indianapolis, Ind., USA).

Figure 4:
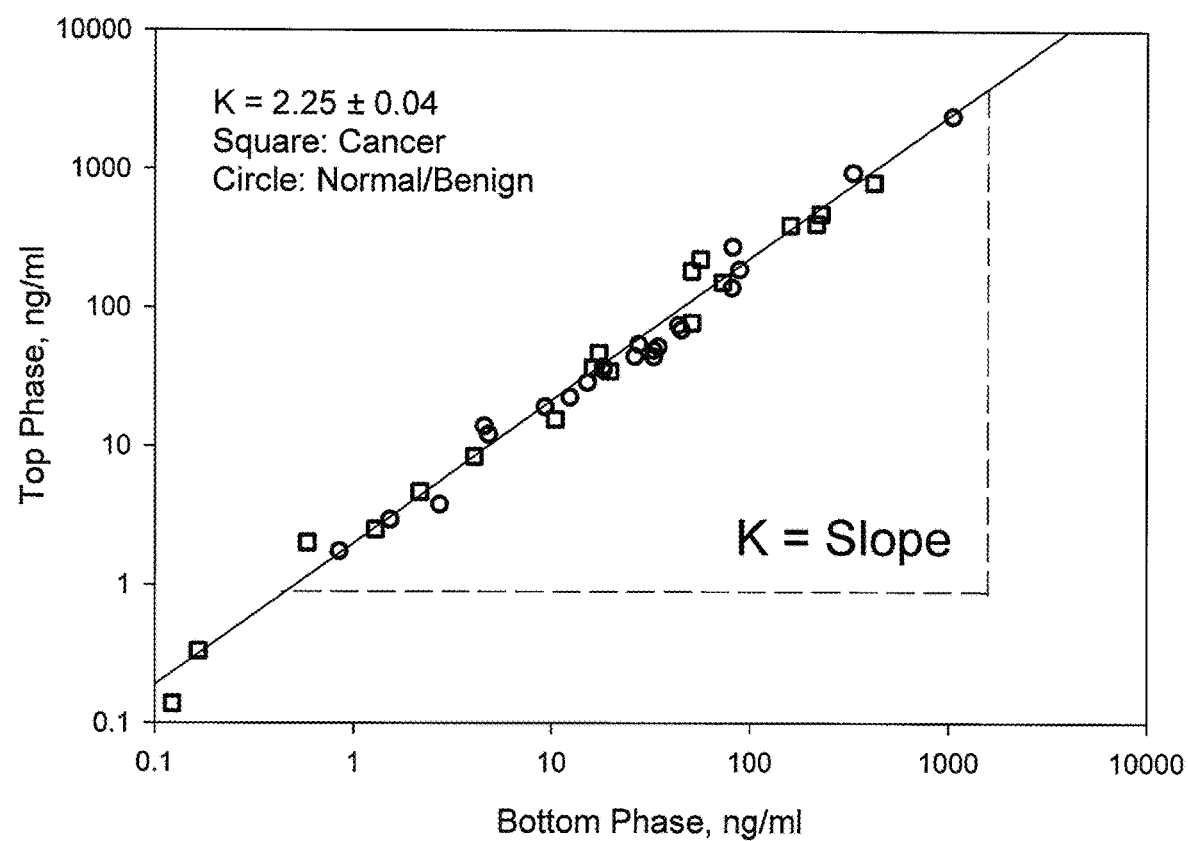
FIG. 4. PSA concentrations in the top and bottom phases for both normal and cancer samples according to one embodiment of the invention, as discussed in Example 4.

The results obtained are plotted in FIG. 4 as the PSA concentrations for different individual patients determined in the top Ficoll-rich phase versus the PSA concentrations for the same individual patients determined in the bottom dextran-rich phase. The data given in FIG. 4 indicated a linear continuous relationship between the PSA concentrations measured for different patients in the upper phase and PSA concentrations for the same patients measured in the bottom phase. The slope of this linear relationship represents the ratio of the PSA concentration in the top phase to that in the bottom phase for each individual patient, which is the PSA relative measure of interaction with the two phases, here referred to as the PSA partition coefficient. These data indicated that the PSA partition coefficient for any specific patient is independent of the total PSA expression level (or concentration) for the same individual. Therefore, if the overall concentration level of PSA is dependent upon physiological conditions other than cancer, for example, a benign prostate condition, its specificity as prostate cancer marker may be reduced (as is the case for PSA). The independence of the PSA relative measure of interaction from its concentration level could be useful for increasing the cancer specificity of PSA, if it has structural or other properties specific to cancer that could be expressed via changes to its relative measure of interaction with systems according to techniques described herein.

Example 5

This example illustrates partitioning of PSA from urine from patients with prostate cancer in aqueous PEG-salt two-phase system differs from that of PSA from urine from patients free of prostate cancer.

Urine samples were collected from patients who were candidates for prostate biopsy based on serum PSA levels above 4 ng/ml or based on other clinical presentations. The urine samples were collected immediately post prostate massage performed by a physician and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use. Urine samples from 9 patients with prostate cancer established by prostate biopsy analysis were thawed and combined to form a "cancer" urine pool sample. Urine samples from patients established to be free of prostate cancer according to results from prostate biopsy analysis were thawed and combined to form a "control" urine pool sample. These pool samples were stored at −80° C. until further use.

Poly(ethylene glycol)-8000 (PEG-8000) (with molecular weight of 8,000) and inorganic salts of ACS reagent grade were purchased from Sigma Chemical Company (St. Louis, Mo., USA) and used without further purification. Stock solutions of individual polymer and inorganic salts in water were prepared gravimetrically and used to form aqueous two-phase system as described below.

The aqueous two-phase system contained 12.60 wt % PEG-8000, 8.90 wt % sodium/potassium phosphate buffer (pH 7.4), and 10.5 wt % NaCl. Each system was prepared by mixing the appropriate amounts of stock polymer, salt and buffer solutions by weight into a 1.2 mL microtube up to a total weight of a system of 0.460 g (volume 0.387 mL) using a MICROLAB 4000 MPH-4 liquid handling robotics workstation (Hamilton Company, Reno, Nev., USA). Urine samples from cancer urine pool and control urine pool in amounts of 0.075 mL were added to each system. The systems were vigorously shaken by vortexing and centrifuged for 60 min at about 2500 rpm in a refrigerated centrifuge at room temperature with a microplate rotor to speed the phase settling. The microtubes were taken out of the centrifuge, and aliquots of 100 ml from the top and the bottom phases were withdrawn and each diluted with 0.400 ml water for PSA concentration analysis.

PSA concentration was determined in each aliquot by an automated enzyme-linked immunosorbent assay (ELISA), Elecsys Total PSA Immunoassay, lower detection limit 0.002 ng/ml; Roche Diagnostics (Indianapolis, Ind., USA).

The results of PSA concentration measurements in the two phases and the PSA partition coefficients calculated as the ratios of the PSA concentration in the top phase to the PSA concentration in the bottom phase are presented in Table 4.

TABLE 4

|  | Control urine* pool | Prostate cancer urine* pool |
| --- | --- | --- |
| Sample PSA level | 12,430** ng/ml | 4,560** ng/ml |
| Top phase PSA concentration | 610.00** ng/ml | 199.00** ng/ml |
| Bottom phase PSA concentration | 46.16 ng/ml | 24.19 ng/ml |
| PSA partition coefficient, K | 13.2 | 8.2 |

*Urine was collected post prostate massage as described above;
**PSA concentrations were measured followed additional 100-fold dilution with universal diluent (Roche Diagnostics).

The results obtained with the pooled urine samples indicated that partition coefficient for PSA from patients with prostate cancer in the aqueous PEG-8000-salt two-phase system used in this example differs from the partition coefficient of PSA from patients free of prostate cancer. Therefore, the particular system used in this example can be useful for a method for detecting prostate cancer according to techniques and methods described in the present invention.

Example 6

This example illustrates that partitioning of PSA from urine from patients with prostate cancer in aqueous PEG-dextran two-phase system differs from that of PSA from urine from patients free of prostate cancer.

Urine samples were collected from patients who were candidates for prostate biopsy based on serum PSA levels above 4 ng/ml or based on other clinical presentations. The urine samples were collected immediately post prostate massage performed by a physician and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use. Urine samples from 9 patients with prostate cancer established by prostate biopsy analysis were thawed and combined to form a "cancer" urine pool sample. Urine samples from patients established to be free of prostate cancer according to results from prostate biopsy analysis were thawed and combined to form a "control" urine pool sample. These pool samples were stored at −80° C. until further use.

Dextran-75 (with molecular weight of 60,000 to 90,000) was purchased from USB Corporation (Cleveland, Ohio, USA) and used without further purification. Poly(ethylene glycol)-600 (PEG-600) (with molecular weight of 600) and inorganic salts of ACS reagent grade were purchased from Sigma Chemical Company (St. Louis, Mo., USA) and used without further purification. S tock solutions of individual polymers and inorganic salts in water were prepared gravimetrically and used to form aqueous two-phase system as described below.

The aqueous two-phase system contained 11.90 wt % dextran-75, 15.7 wt % PEG-600, 0.15 M sodium sulfate in 0.01 M sodium phosphate buffer (pH 7.4). Each system was prepared by mixing the appropriate amounts of stock polymer, salt and buffer solutions by weight into a 1.2 mL microtube up to a total weight of a system of 0.433 g (volume 0.394 mL) using a MICROLAB 4000 MPH-4 liquid handling robotics workstation (Hamilton Company, Reno, Nev., USA). Urine samples from cancer urine pool and control urine pool in amounts of 0.075 mL were added to each system. The systems were vigorously shaken by vortexing and centrifuged for 60 min at about 2500 rpm in a refrigerated centrifuge at room temperature with a microplate rotor to speed the phase settling. The microtubes were taken out of the centrifuge, and aliquots of 100 microliter from the top and the bottom phases were withdrawn and each diluted with 0.400 ml water for PSA concentration analysis.

PSA concentration was determined in each aliquot by an automated enzyme-linked immunosorbent assay (ELISA) Elecsys Total PSA Immunoassay; lower detection limit 0.002 ng/ml; (Roche Diagnostics, Indianapolis, Ind., USA).

The results of PSA concentration measurements in the two phases and the PSA partition coefficients calculated as the ratios of the PSA concentration in the top phase to the PSA concentration in the bottom phase are presented in Table 5.

TABLE 5

|  | Control urine* pool | Prostate cancer urine* pool |
| --- | --- | --- |
| Sample PSA level | 12,430** ng/ml | 4,560** ng/ml |
| Top phase PSA concentration | 366.00** ng/ml | 24.78 ng/ml |
| Bottom phase PSA concentration | 20.96 ng/ml | 3.62 ng/ml |
| PSA partition coefficient, K | 17.5 | 6.8 |

*Urine was collected post prostate massage as described above;
**PSA concentrations were measured followed additional 100-fold dilution with universal diluent (Roche Diagnostics).

The results obtained with the pooled urine samples indicated that partition coefficient for PSA from patients with prostate cancer in the aqueous PEG-dextran two-phase system used in this example differs from the partition coefficient of PSA from patients free of prostate cancer. Therefore, the particular system described in the present example can be used for diagnostics purposes according to techniques described in the present invention.

Example 7

This example illustrates partitioning of PSA from urine from patients with prostate cancer in aqueous dextran-Ficoll-phosphate buffer two-phase systems of different salt compositions differs from that of PSA from urine from patients free of prostate cancer.

Urine samples were collected from patients who were candidates for prostate biopsy based on serum PSA levels above 4 ng/ml or based on other clinical presentations. The urine samples were collected immediately post prostate massage performed by a physician and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use. Urine samples from 9 patients with prostate cancer established by prostate biopsy analysis were thawed and combined to form a "cancer" urine pool sample. Urine samples from patients established to be free of prostate cancer according to results from prostate biopsy analysis were thawed and combined to form a "control" urine pool sample. These pool samples were stored at −80° C. until further use.

Dextran-75 (with molecular weight of 60,000 to 90,000) was purchased from USB Corporation (Cleveland, Ohio, USA) and used without further purification. Ficoll-70 (with molecular weight of about 70,000) was purchased from GE Healthcare Bio-Sciences Corp. (Piscataway, N.J., USA) and used without further purification. All inorganic salts of ACS reagent grade were purchased from Sigma Chemical Company (St. Louis, Mo., USA) and used without further purification. Stock solutions of individual polymers and inorganic salts in water were prepared gravimetrically and used to form aqueous two-phase system as described below.

The aqueous two-phase system contained 18.00 wt % Ficoll-70, 13.0 wt % dextran-75, 2.2 wt % (0.15 M) sodium/potassium phosphate buffer (pH 7.4). Each system was prepared by mixing the appropriate amounts of stock polymer, salt and buffer solutions by weight into a 1.2 mL microtube up to a total weight of a system of 0.421 g (volume 0.359 mL) using a MICROLAB 4000 MPH-4 liquid handling robotics workstation (Hamilton Company, Reno, Nev., USA). Urine samples from cancer urine pool and control urine pool in amounts of 0.075 mL were added to each system. The systems were vigorously shaken by vortexing and centrifuged for 60 min at about 2,500 rpm in a refrigerated centrifuge at room temperature with a microplate rotor to speed the phase settling. The microtubes were taken out of the centrifuge, and aliquots of 100 microliter from the top and the bottom phases were withdrawn and each diluted with 0.400 ml water for PSA concentration analysis.

PSA concentration was determined in each aliquot by an automated enzyme-linked immunosorbent assay (ELISA), Elecsys Total PSA Immunoassay, lower detection limit 0.002 ng/ml (Roche Diagnostics, Indianapolis, Ind., USA).

The results of PSA concentration measurements in the two phases and the PSA partition coefficients calculated as the ratios of the PSA concentration in the top phase to the PSA concentration in the bottom phase are presented in Table 6.

TABLE 6

|  | Control urine* pool | Prostate cancer urine* pool |
|---|---|---|
| Sample PSA level | 12,430** ng/ml | 4,560** ng/ml |
| Top phase PSA concentration | 243.00** ng/ml | 66.61 ng/ml |
| Bottom phase PSA concentration | 11.48 ng/ml | 4.35 ng/ml |
| PSA partition coefficient, K | 21.2 | 15.3 |

*Urine was collected post prostate massage as described above;
**PSA concentrations were measured followed additional 100-fold dilution with universal diluent (Roche Diagnostics).

The results obtained with the pooled urine samples indicated that partition coefficient for PSA from patients with prostate cancer in the aqueous dextran-Ficoll-phosphate buffer two-phase system used in this example differs from the partition coefficient of PSA from patients free of prostate cancer. Therefore, the particular system described in the present example can be used for diagnostics purposes according to techniques described in the present invention.

Example 8

This example illustrates partitioning of PSA from urine from patients with prostate cancer in aqueous dextran-Ficoll-sodium sulfate-phosphate buffer two-phase systems of different salt compositions differs from that of PSA from urine from patients free of prostate cancer.

Urine samples were collected from patients who were candidates for prostate biopsy based on serum PSA levels above 4 ng/ml or based on other clinical presentations. The urine samples were collected immediately post prostate massage performed by a physician and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use. Urine samples from 9 patients with prostate cancer established by prostate biopsy analysis were thawed and combined to form a "cancer" urine pool sample. Urine samples from patients established to be free of prostate cancer according to results from prostate biopsy analysis were thawed and combined to form a "control" urine pool sample. These pool samples were stored at −80° C. until further use.

Dextran-75 (with molecular weight of 60,000 to 90,000) was purchased from USB Corporation (Cleveland, Ohio, USA) and used without further purification. Ficoll-70 (with molecular weight of about 70,000) was purchased from GE Healthcare Bio-Sciences Corp. (Piscataway, N.J., USA) and used without further purification. All inorganic salts of ACS reagent grade were purchased from Sigma Chemical Company (St. Louis, Mo., USA) and used without further purification. Stock solutions of individual polymers and inorganic salts in water were prepared gravimetrically and used to form aqueous two-phase system as described below.

The aqueous two-phase system contained 18.00 wt % Ficoll-70, 13.0 wt % dextran-75, 0.15 M sodium sulfate, and 0.01 M sodium phosphate buffer (pH 7.4). Each system was prepared by mixing the appropriate amounts of stock polymer, salt and buffer solutions by weight into a 1.2 mL microtube up to a total weight of a system of 0.431 g (volume 0.367 mL) using a MICROLAB 4000 MPH-4 liquid handling robotics workstation (Hamilton Company, Reno, Nev., USA). Urine samples from cancer urine pool and control urine pool in amounts of 0.075 mL were added to each system. The systems were vigorously shaken by vortexing and centrifuged for 60 min at about 2,500 rpm in a refrigerated centrifuge at room temperature with a microplate rotor to speed the phase settling. The microtubes were taken out of the centrifuge, and aliquots of 100 microliter from the top and the bottom phases were withdrawn and each diluted with 0.400 ml water for PSA concentration analysis.

PSA concentration was determined in each aliquot by an automated enzyme-linked immunosorbent assay (ELISA), Elecsys Total PSA Immunoassay, lower detection limit 0.002 ng/ml (Roche Diagnostics, Indianapolis, Ind., USA).

The results of PSA concentration measurements in the two phases and the PSA partition coefficients calculated as the ratios of the PSA concentration in the top phase to the PSA concentration in the bottom phase are presented in Table 7.

TABLE 7

|  | Control urine* pool | Prostate cancer urine* pool |
|---|---|---|
| Sample PSA level | 12,430** ng/ml | 4,560** ng/ml |
| Top phase PSA concentration | 298.00** ng/ml | 159.00** ng/ml |
| Bottom phase PSA concentration | 64.95 ng/ml | 13.01 ng/ml |

TABLE 7-continued

|  | Control urine* pool | Prostate cancer urine* pool |
|---|---|---|
| PSA partition coefficient, K | 4.6 | 12.2 |

*Urine was collected post prostate massage as described above;
**PSA concentrations were measured followed additional 100-fold dilution with universal diluent (Roche Diagnostics).

The results obtained with the pooled urine samples indicated that partition coefficient for PSA from patients with prostate cancer in the aqueous dextran-Ficoll-sodium sulfate-phosphate buffer two-phase system used in this example differs from the partition coefficient of PSA from patients free of prostate cancer. Therefore, the particular system described in the present example can be used for diagnostics purposes according to techniques described in the present invention.

Example 9

This example illustrates partitioning of PSA from urine from individual patients with prostate cancer in aqueous dextran-Ficoll-sodium isothiocyanate-phosphate buffer two-phase systems of different salt compositions differs from that of PSA from urine from patients free of prostate cancer.

Urine samples were collected from patients who were candidates for prostate biopsy based on serum PSA levels above 4 ng/ml or based on other clinical presentations. The urine samples were collected immediately post prostate massage performed by a physician and included 4 passes over the prostate with pressure lasting at least 5 seconds. Each urine sample was transferred into 5 ml polypropylene tube, centrifuged for 10 min at 3,000 rpm, supernatant separated, aliquoted by 0.5 ml, placed into Eppendorf microtubes, and stored at −80° C. until further use.

Dextran-75 (with molecular weight of 60,000 to 90,000) was purchased from USB Corporation (Cleveland, Ohio, USA) and used without further purification. Ficoll-70 (with molecular weight of about 70,000) was purchased from GE Healthcare Bio-Sciences Corp. (Piscataway, N.J., USA) and used without further purification. All inorganic salts of ACS reagent grade were purchased from Sigma Chemical Company (St. Louis, Mo., USA) and used without further purification. Stock solutions of individual polymers and inorganic salts in water were prepared gravimetrically and used to form aqueous two-phase system as described below.

The aqueous two-phase system contained 18.00 wt % Ficoll-70, 13.00 wt % dextran-75, and 0.15 M NaSCN in 0.010 M sodium phosphate buffer (pH 7.4). Each system was prepared by mixing the appropriate amounts of stock polymer, salt and buffer solutions by weight into a 1.2 mL microtube up to a total weight of a system of 0.426 g (volume 0.369 mL) using a MICROLAB 4000 MPH-4 liquid handling robotics workstation (Hamilton Company, Reno, Nev., USA). Urine samples from individual patients in amounts of 0.075 mL were added to each system. The systems were vigorously shaken by vortexing and centrifuged for 60 min at about 2,500 rpm in a refrigerated centrifuge at room temperature with a microplate rotor to speed the phase settling. The microtubes were taken out of the centrifuge, and aliquots of 100 microliter from the top and the bottom phases were withdrawn and each diluted with 0.400 ml water for PSA concentration analysis.

PSA concentration was determined in each aliquot by an automated enzyme-linked immunosorbent assay (ELISA), Elecsys Total PSA Immunoassay, lower detection limit 0.002 ng/ml (Roche Diagnostics, Indianapolis, Ind., USA).

The results obtained are presented in Table 8 as the PSA concentrations for different individual patients measured in serum, and concentrations determined in the top Ficoll-rich phase versus the PSA concentrations for the same individual patients determined in the bottom dextran-rich phase.

TABLE 8

| Patient # | Serum total PSA, ng/ml | No prostate cancer PSA Partition coefficient, K value | Prostate cancer PSA Partition coefficient, K value |
|---|---|---|---|
| 1 | 4.12 | 1.06 |  |
| 2 | 13.59 | 1.23 |  |
| 3 | 11.15 |  | 1.42 |
| 4 | 4.9 |  | 1.69 |
| 5** | 7.74 |  | 1.65 |
| 6** | 4.58 |  | 1.34 |
| 7 | 5.7 |  | 1.73 |
| 11 | 10.3 | 1.62 |  |
| 12** | 15.6 |  | 1.61 |
| 13 | 6.06 |  | 1.86 |
| 14 | 6.6 | 1.43 |  |
| 15 | 4.25 |  | 1.68 |
| 16 | 6.6 | 1.36 |  |
| 17 | 5.1 | 1.44 |  |
| 18 | 3.64 |  | 1.51 |
| 19 | 4.65 |  | 1.61 |
| 20 | 9.36 | 1.60 |  |
| 22 | 7.98 |  | 1.46 |
| 23 | 4.05 | 1.13 |  |
| 26 | 4.7 | 1.30 |  |

*Urine was collected post prostate massage as described above;
**patients were established to have benign prostate disease by prostate biopsy analysis.

Figure 5:
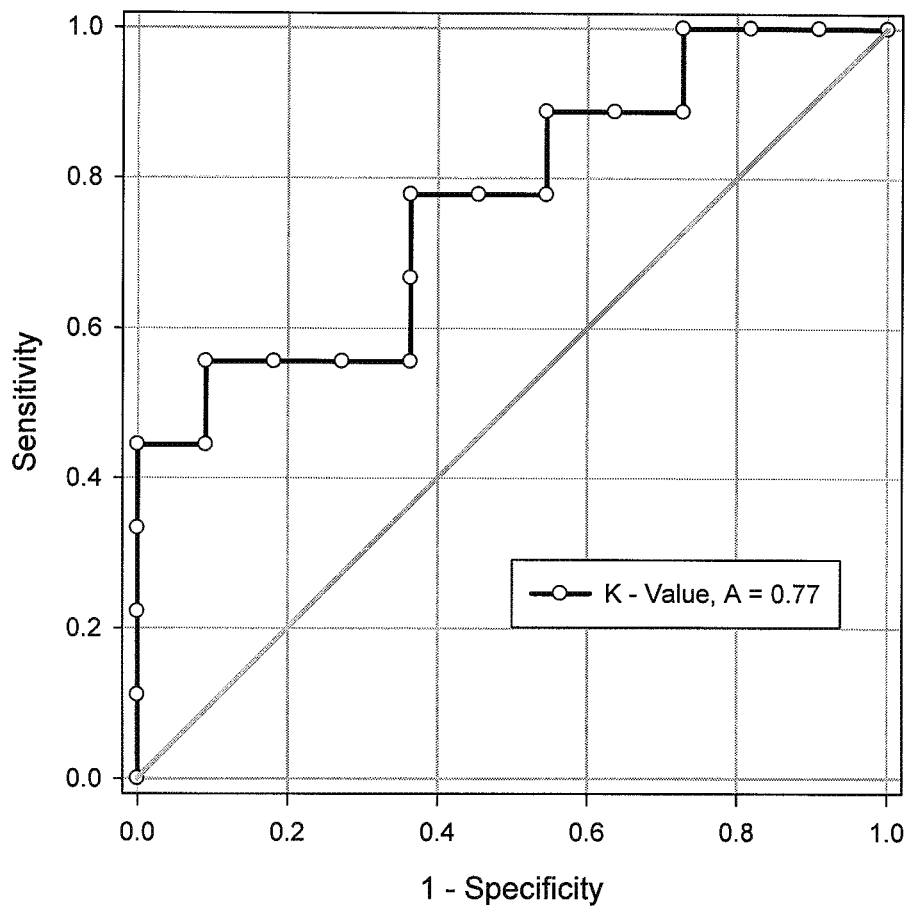
FIG. 5 is the Receiver-Operating Characteristics (ROC) curve corresponding to clinical data described in Example 8, in another embodiment of the invention.

The data in Table 8 were subsequently processed using standard statistical techniques for detecting statistically significance between cancer and normal samples, and for obtaining the relationship between specificity and sensitivity. FIG. 5 depicts the ROC (Receiver-Operator Characteristics) curve calculated using SigmaPlot 10 statistical software (Systat Software, San Jose, Calif., USA). The data indicate a departure from the diagonal, with area under the curve of 0.77 (P=0.044). The ROC curve provides a relationship between sensitivity and specificity for a given cut-off value in the partition coefficient. For example, a diagnostics test could be devised to further stratify patients with elevated PSA levels and/or other clinical presentations into those who should receive biopsy and those who should be actively monitored. For such a clinical application, a cut-off value for the partition coefficient could be selected at 1.3, resulting in 100% specificity (or false positive fraction). If the sensitivity of the test is provided a priori by other means (e.g., PSA level, velocity and other clinical presentations), then the test using partition coefficient as described in the present invention can be used to reduce the number of false positive biopsies.

While several embodiments of the invention have been described and illustrated herein, those of ordinary skill in the art will readily envision a variety of other means and structures for performing the functions and/or obtaining the results or advantages described herein, and each of such variations or modifications is deemed to be within the scope of the present invention. More generally, those skilled in the art would readily appreciate that all parameters, dimensions, materials, and configurations described herein are meant to be exemplary and that actual parameters, dimensions, materials, and configurations will depend upon specific applications for which the teachings of the present invention are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described. The present invention is directed to each individual feature, system, material and/or method described herein. In addition, any combination of two or more such features, systems, materials and/or methods, if such features, systems, materials and/or methods are not mutually inconsistent, is included within the scope of the present invention.

The definitions, as used herein, should be understood to control over dictionary definitions, definitions in documents incorporated by reference, and/or ordinary meanings of the defined terms.

It should also be understood that, unless clearly indicated to the contrary, in any methods claimed herein that include more than one act, the order of the acts of the method is not necessarily limited to the order in which the acts of the method are recited.

In the claims (as well as in the specification above), all transitional phrases such as "comprising," "including," "carrying," "having," "containing," "involving," and the like are to be understood to be open-ended, i.e. to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method for identifying one or more tools for determining ovarian cancer, comprising:
   partitioning blood serum from a first subject having ovarian cancer in at least a first phase and a second phase of a first aqueous multi-phase system, wherein the second phase is immiscible with the first phase at equilibrium;
   determining a relative measure of interaction with the first and second phases of the first system, of a species within the blood serum selected from the group consisting of EGFR, IL-8, G-CSF, sIL-6R, IGFBP-1, bFGF, and RANTES;
   determining a relative measure of interaction of the species with the first and second phases of the first system;
   determining a difference in the relative measure of interaction of the species of the first subject with the first and second phases of the first system, versus the relative measure of interaction of the species of the second subject with the first and second phases of the first system; and
   based upon the difference, selecting the first system as a tool for determining ovarian cancer in a subject based upon the determination of the relative measures of interaction of the species.

2. The method of claim 1, further comprising determining a difference in the relative measure of interaction of the species of the first subject versus the relative measure of interaction of the species of the second subject, in both the first system and a different, second aqueous multi-phase system.

3. The method of claim 1, comprising determining a difference in the relative measure of interaction of the species of the first subject versus the relative measure of interaction of the species of the second subject, in only a single aqueous multi-phase system.

4. The method of claim 1, further comprising:
   determining a relative measure of interaction of the species of the first subject, with at least a first phase and a second phase of a second aqueous multi-phase system;
   determining a relative measure of interaction of the species of the second subject, with the first and second phases of the second system;
   determining a difference in the relative measure of interaction of the species of the first subject with the first and second phases of the second system, versus the relative measure of interaction of the species of the second subject with the first and second phases of the second system; and
   based upon the difference, selecting the second system as a tool, in conjunction with the first system, for determining ovarian cancer.

5. The method of claim 1, further comprising:
   determining a relative measure of interaction of the species of the first subject, with at least a first phase and a second phase of a third aqueous multi-phase system;
   determining a relative measure of interaction of the species of the second subject, with the first and second phases of the third system;
   determining a lack of significant difference in the relative measure of interaction of the species of the first subject with the first and second phases of the third system, versus the relative measure of interaction of the species of the second subject with the first and second phases of the third system; and
   based upon the lack of significant difference, rejecting the third system as a tool for determining ovarian cancer.

6. The method of claim 1, wherein the first aqueous multi-phase system comprises a polymer.

7. The method of claim 1, wherein the first aqueous multi-phase system comprises a salt.

8. The method of claim 1, wherein the first aqueous multi-phase system comprises a surfactant.

9. The method of claim 1, wherein the relative measure of interaction comprises a partition coefficient.

10. The method of claim 1, wherein the first subject is human.

11. A method of determining ovarian cancer, comprising:
    partitioning blood serum from a subject in at least a first phase and a second phase of a first aqueous multi-phase system, wherein the second phase is immiscible with the first phase at equilibrium;
    determining a relative measure of interaction of a species within the blood serum selected from the group consisting of EGFR, IL-8, G-CSF, sIL-6R, IGFBP-1, bFGF, and RANTES with the first and second phases of the first system; and
    from the process of determining the relative measure of interaction of the species with the first and second phases of the first system, determining whether the subject has ovarian cancer.

12. The method of claim 11, comprising determining whether the subject has ovarian or has an elevated risk of ovarian cancer.

13. The method of claim 11, comprising determining malignancy of the ovarian cancer in the subject.

14. The method of claim 11, comprising determining a response to treatment of the ovarian cancer of the subject.

15. The method of claim 11, comprising determining a metastatic state of the ovarian cancer.

16. The method of claim 11, comprising determining an aggressiveness potential of the ovarian cancer.

17. The method of claim 11, wherein the first aqueous multi-phase system comprises a polymer.

18. The method of claim 11, wherein the first aqueous multi-phase system comprises a salt.

19. The method of claim 11, wherein the first aqueous multi-phase system comprises a surfactant.

20. The method of claim 11, wherein the relative measure of interaction comprises a partition coefficient.

* * * * *